(12) United States Patent
Mou et al.

(10) Patent No.: US 10,969,310 B2
(45) Date of Patent: Apr. 6, 2021

(54) PARTICLE DETECTING MODULE

(71) Applicant: Microjet Technology Co., Ltd., Hsinchu (TW)

(72) Inventors: Hao-Jan Mou, Hsinchu (TW); Chi-Feng Huang, Hsinchu (TW); Yung-Lung Han, Hsinchu (TW); Hsuan-Kai Chen, Hsinchu (TW)

(73) Assignee: MICROJET TECHNOLOGY CO., LTD., Hsinchu (TW)

( * ) Notice: Subject to any disclaimer, the term of this patent is extended or adjusted under 35 U.S.C. 154(b) by 182 days.

(21) Appl. No.: 16/263,979

(22) Filed: Jan. 31, 2019

(65) Prior Publication Data
US 2019/0331565 A1  Oct. 31, 2019

(30) Foreign Application Priority Data

Apr. 27, 2018 (TW) .................................. 107114584
Sep. 21, 2018 (TW) .................................. 107133514

(51) Int. Cl.
| | | |
|---|---|---|
| *G01N 1/44* | (2006.01) | |
| *B01D 53/00* | (2006.01) | |
| *G01N 15/02* | (2006.01) | |
| *G01N 15/06* | (2006.01) | |
| *G01N 15/14* | (2006.01) | |
| *G01N 33/00* | (2006.01) | |

(52) U.S. Cl.
CPC ............. *G01N 1/44* (2013.01); *B01D 53/005* (2013.01); *G01N 15/0211* (2013.01); *G01N 15/0606* (2013.01); *G01N 15/0656* (2013.01); *G01N 15/1404* (2013.01); *G01N 33/0014* (2013.01); *G01N 33/0022* (2013.01); *G01N 33/0073* (2013.01)

(58) Field of Classification Search
CPC .. G01N 1/44; G01N 15/0211; G01N 15/0606; G01N 15/0656; G01N 15/1404; G01N 33/0014; G01N 33/0022; G01N 33/0073; B01D 53/005
USPC ...................................................... 73/863.12
See application file for complete search history.

(56) References Cited

U.S. PATENT DOCUMENTS

2017/0115196 A1   4/2017  Tsuboi et al.
2019/0302076 A1*  10/2019 Mou .................. G01N 33/0016

FOREIGN PATENT DOCUMENTS

| CN | 202512041 U | 10/2012 |
|---|---|---|
| CN | 105067778 A | 11/2015 |
| TW | M554165 U | 1/2018 |

(Continued)

OTHER PUBLICATIONS

Extended European Search Report for European Application No. 19154741.3, dated Sep. 16, 2019.

*Primary Examiner* — Tarun Sinha
(74) *Attorney, Agent, or Firm* — Birch, Stewart, Kolasch & Birch, LLP

(57) ABSTRACT

A particle detecting module is disclosed and includes a main body, which is consist of an air guiding part and a detecting part, by driving a plurality of heating elements disposed within a plurality of storage chambers of the air guiding part, air inside these storage chambers is heated and the moisture of the air is removed, and then the air is transported to the detecting part, so that a sensor of the detecting part could detect the sizes and the concentrations of the suspended particles, and the interference of the humidity is reduced.

16 Claims, 20 Drawing Sheets

(56) References Cited

FOREIGN PATENT DOCUMENTS

| | | | |
|---|---|---|---|
| TW | M554535 | U | 1/2018 |
| TW | M558353 | U | 4/2018 |

\* cited by examiner

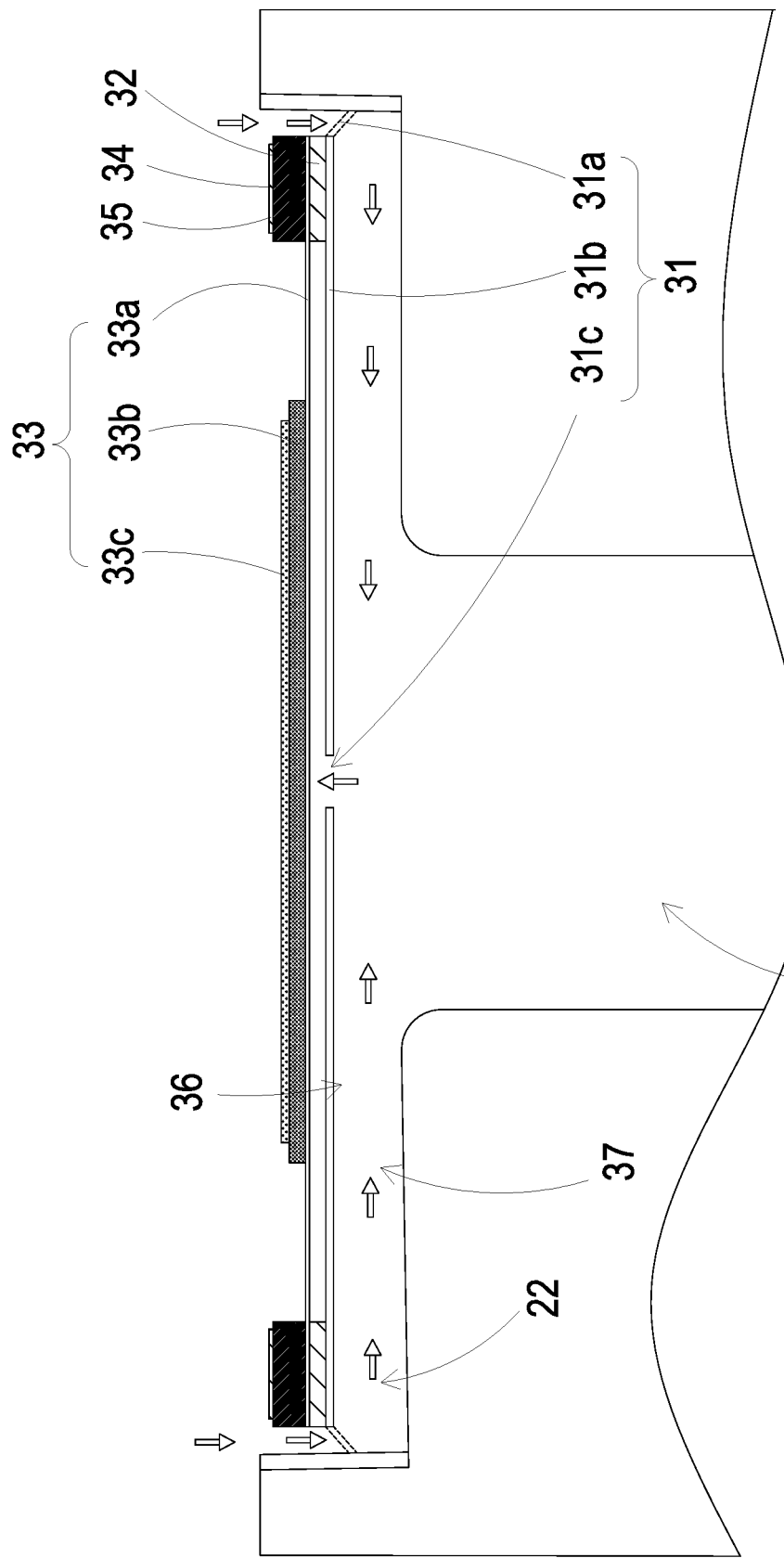

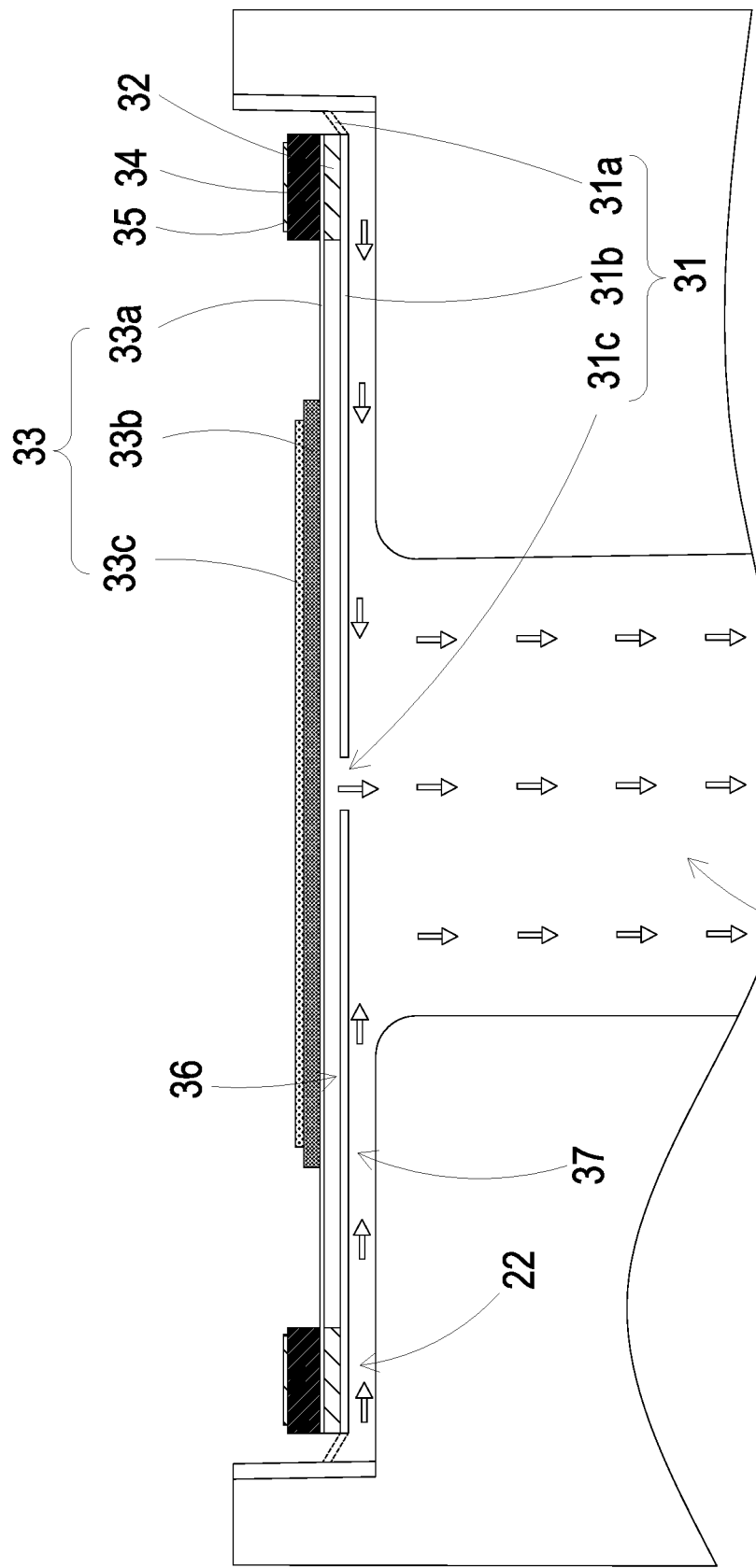

PARTICLE DETECTING MODULE

FIELD OF THE DISCLOSURE

The present disclosure relates to a particle detecting module, and more particularly to a particle detecting module capable of maintaining a standard humidity level of the air and capable of being assembled to a thin-type portable device for air monitoring.

BACKGROUND OF THE DISCLOSURE

Suspended particles refer to solid particles or droplets contained in the air. Fine suspended particles are so small that they can easily enter the lungs of the human body since it is difficult to obstruct them by the nasal hair in the nasal cavity. The fine suspended particles entered in the human body can cause inflammation, asthma or cardiovascular disease in the lungs. If other pollutants are attached to the suspended particles, the injury to the respiratory system of the human body can be even worse.

Mostly, the conventional gas detecting modules are set in fixed-point type, and only the air information around the air observation station can be measured. In other words, the concentration of suspended particles cannot be provided at anytime and anywhere. In addition, the interference caused by water vapor with the detection of suspended particles is not prevented. In a high-humidity environment, the suspended particles would be surrounded by water vapor and have larger volume. Under this circumstance, the light transmittance thereof becomes insufficient, and the small water molecules (water droplets) in the air are increased, which will directly affect the accuracy of the detection.

Therefore, there is need to provide a particle detecting module to achieve the purposes of detecting the suspended particles at anytime and anywhere, eliminating the influence of humidity environment relative to the detection results, improving the detecting efficiency and detecting the suspended particles correctly, and which is an urgent need for the industry to solve.

SUMMARY OF THE DISCLOSURE

An object of the present disclosure is to provide a particle detecting module applied to a thin-type portable device for detecting the suspended particle in the air. The particle detecting module inhales air into the first compartment through the inlet, and the air is heated in the first compartment so as to maintain the air at a standard humidity level in the first compartment for detecting and improve the detecting efficiency of gas sensor. In addition, the main body of the particle detecting module has a detecting chamber with a one-way opening, so as to allow the air to flow in and flow out in one way for detecting. By utilizing a resonance plate to transport the air through the actuator, the particle detecting module can be applied to a thin-type portable device for instant measuring.

In accordance with an aspect of the present disclosure, there is provided a particle detecting module. The particle detecting module includes a main body, a fine particle detecting base, an actuator and a sensor. The main body includes an air guiding part and a detecting part combined with each other. The air guiding part includes a plurality of storage chambers and a plurality of airflow channels. Each storage chamber includes an inlet aperture, a heat-dissipation aperture, an outlet aperture and a heating element, wherein the heating element heats the air within the corresponding storage chamber to dehumidify, water vapor generated by heating in the corresponding storage chamber is discharged out through the heat-dissipation aperture and the dehumidified air is discharged out through the outlet aperture. Each two adjacent storage chambers are in fluid communication with each other through the corresponding airflow channel so that the air has been dehumidified in one of the storage chambers can be transported into another storage chamber through the corresponding airflow channel to perform a further dehumidification operation. The detecting part includes an inlet compartment, an outlet compartment, a carrying partition and a discharging aperture. The inlet compartment and the outlet compartment are divided through the carrying partition. The discharging aperture is in fluid communication with the outlet compartment and the exterior of the detecting part. The carrying partition has a communication opening in fluid communication between the inlet compartment and the outlet compartment. The fine particle detecting base is disposed in the inlet compartment and has a detecting channel and a receiving slot. The receiving slot is disposed at one end of the detecting channel and in fluid communication with the detecting channel. The actuator is disposed in the fine particle detecting base to control air to flow from the inlet compartment into the detecting channel, be transported to the outlet compartment through the communication opening and be discharged out through the discharging aperture, so as to achieve air transportation of the detecting part in one way. The sensor is disposed on the carrying partition and located in the detecting channel of the find particle detecting base, to measure a concentration of suspended particles contained in the air flowing into the detecting channel. Thus, when air at a humidity level higher than 40% is inhaled from the exterior into the air guiding part, the air is transported through each of the storage chambers connected in serial to be heated and dehumidified, thereby achieving the humidity level ranged from 10% to 40%. The dehumidified air is transported into the detecting part and transported to the detecting channel as being driven by the actuator so that the sensor measures the concentration of suspended particles contained in the air flowing into the detecting channel accurately.

The above contents of the present disclosure will become more readily apparent to those ordinarily skilled in the art after reviewing the following detailed description and accompanying drawings, in which:

BRIEF DESCRIPTION OF THE DRAWINGS

FIG. 7B and FIG. 7C are schematic views illustrating actions of the actuator according to the first embodiment of the present disclosure;

DETAILED DESCRIPTION OF THE PREFERRED EMBODIMENT

The present disclosure will now be described more specifically with reference to the following embodiments. It is to be noted that the following descriptions of preferred embodiments of this disclosure are presented herein for purpose of illustration and description only. It is not intended to be exhaustive or to be limited to the precise form disclosed.

Figure 1:
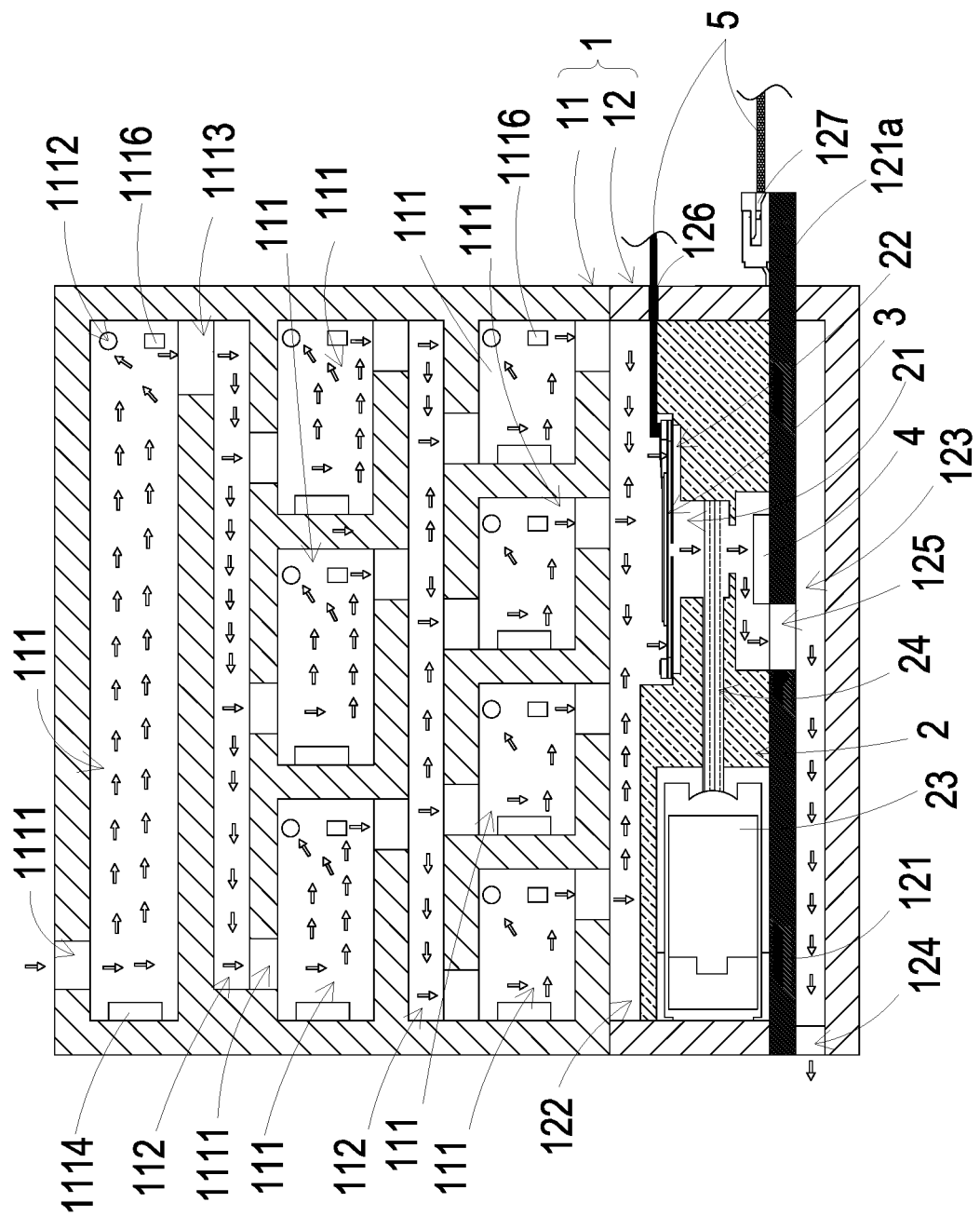
FIG. 1 is a schematic cross-sectional view illustrating a particle detecting module according to a first embodiment of the present disclosure.
Figure 4:
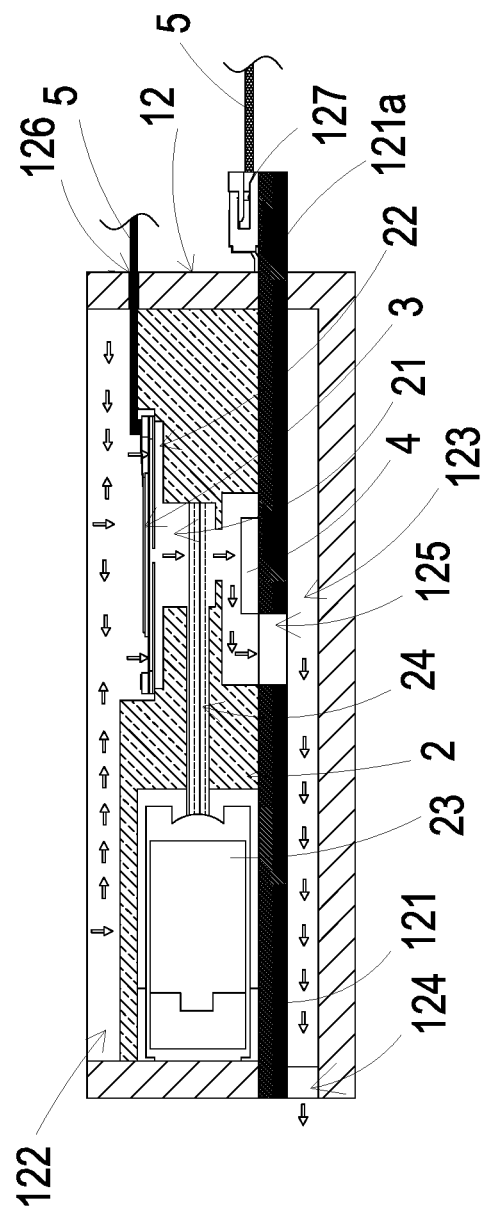
FIG. 4 is a schematic cross-sectional view illustrating the detecting part according to the first embodiment of the present disclosure.

Please refer to FIG. 1 and FIG. 4. The present disclosure provides a particle detecting module including at least one main body 1, at least one fine particle detecting base 2, at least one actuator 3, at least one sensor 4, at least one air guiding part 11, at least one detecting part 12, a plurality of storage chambers 111, at least one inlet aperture 1111, at least one heat-dissipation aperture 1112, at least one outlet aperture 1113, at least one heating element 1114, a plurality of airflow channels 112, at least one carrying partition 121, at least one inlet compartment 122, at least one outlet compartment 123, at least one discharging aperture 124, at least one communication opening 125, at least one detecting channel 21 and at least one receiving slot 22. The numbers of the main body 1, the fine particle detecting base 2, the actuator 3, the sensor 4, the air guiding part 11, the detecting part 12, the inlet aperture 1111, the heat-dissipation aperture 1112, the outlet aperture 1113, the heating element 1114, the carrying partition 121, the inlet compartment 122, the outlet compartment 123, the discharging aperture 124, the communication opening 125, the detecting channel 21 and the receiving slot 22 are exemplified by one for each respectively in the following embodiments but not limited thereto. It is noted that each of the main body 1, the fine particle detecting base 2, the actuator 3, the sensor 4, the air guiding part 11, the detecting part 12, the inlet aperture 1111, the heat-dissipation aperture 1112, the outlet aperture 1113, the heating element 1114, the carrying partition 121, the inlet compartment 122, the outlet compartment 123, the discharging aperture 124, the communication opening 125, the detecting channel 21 and the receiving slot 2 can also be provided in plural numbers.

Figure 2:
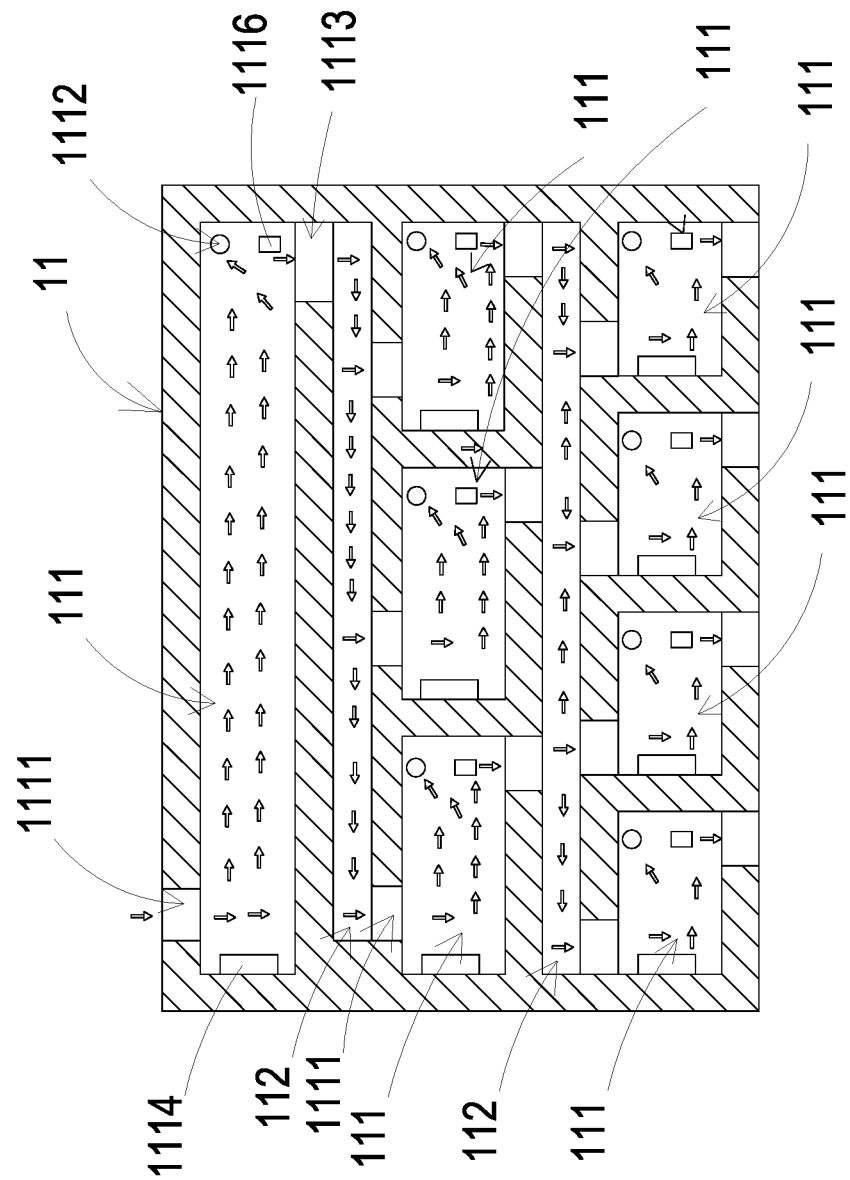
FIG. 2 is a schematic cross-sectional view illustrating the air guiding part according to the first embodiment of the present disclosure.

The present disclosure provides a particle detecting module. Please refer to FIGS. 1 to 3. According to a first embodiment of the present disclosure, the particle detecting module includes a main body 1, a fine particle detecting base 2, an actuator 3 and a sensor 4. The main body 1 includes an air guiding part 11 and a detecting part 12 which are combined with each other. The air guiding part 11 includes a plurality of storage chambers 111 and a plurality of airflow channels 112. Each storage chamber 111 includes an inlet aperture 1111, a heat-dissipation aperture 1112, an outlet aperture 1113 and a heating element 1114. After the air is inhaled into the storage chamber 111 through the inlet aperture 1111, the heating element 1114 heats the air in the storage chamber 111 to achieve a heating and dehumidification operation, and the water vapor generated thereby is discharged out from the storage chamber 111 through the heat-dissipation aperture 1112. Finally, the heated and dehumidified air is discharged out through the outlet aperture 1113. Each airflow channel 112 is connected between two adjacent storage chambers 111. Namely, each two adjacent storage chambers 112 are in fluid communication with each other through a corresponding one of the airflow channels 112. Thus, after the air in each storage chamber 111 is dehumidified, the dehumidified air is guided into an adjacent storage chamber 111 through the corresponding airflow channel 112 to be dehumidified again.

Please refer to FIGS. 1 and 4. The detecting part 12 includes an inlet compartment 122, an outlet compartment 123, a carrying partition 121 and a discharging aperture 124. The inlet compartment 122 and the outlet compartment 123 are divided through the carrying partition 121. The discharging aperture 124 is in fluid communication with the outlet compartment 123 and the exterior of the main body 1. The carrying partition 121 has a communication opening 125 in fluid communication between the inlet compartment 122 and the outlet compartment 123.

The fine particle detecting base 2 is disposed in the inlet compartment 122. In the embodiment, the fine particle detecting base 2 is disposed on the carrying partition 121 and received within the inlet compartment 122. The fine particle detecting base 2 has a detecting channel 21 and a receiving slot 22. The receiving slot 22 is located at one end of the detecting channel 21 to be in fluid communication with the detecting channel 21. Another end of the detecting channel 21 is in fluid communication with the communication opening 125 of the carrying partition 121.

The actuator 3 is disposed within the receiving slot 22 of the fine particle detecting base 2 and covers the receiving slot 22. The actuator 3 is configured to drive the air to flow from the inlet compartment 122 into the detecting channel 21, then to the outlet compartment 123 through the communication opening 125 and discharged out through the discharging aperture 124, thereby achieving unidirectional air transportation in the detecting part 12. The sensor 4 is disposed on the carrying partition 121 and located in the detecting channel 21 of the fine particle detecting base 2, to measure a concentration of the suspended particles contained in the air within the detecting channel 21. The detecting channel 21 is in communication with the inlet compartment 122 so that the air can be inhaled directly to the detecting channel 21 without interference. As a result, the air is guided into the detecting channel 21 at a higher speed. Since the air guided into the detecting channel 21 is measured by the sensor 4, the efficiency of detection is also enhanced thereby.

Please refer to FIGS. 1 and 4. The fine particle detecting base 2 further includes a laser emitter 23 and a light-beam channel 24. The laser emitter 23 is electrically connected to the carrying partition 121 and is disposed adjacent to the light-beam channel 24, to emit a light beam into the light-beam channel 24. The light-beam channel 24 is in communication with the detecting channel 21 to allow the light bam emitted from the laser emitter 23 to irradiate an inner space of the detecting channel 21. When the air within the detecting channel 21 is irradiated by the light beam, the suspended particles contained in the air are irradiated to generate scattering light spots projected on the sensor 4. The sensor 4 receives the scattering light sports generated by the suspended particles and measures the sizes and concentrations of the suspended particles. The sensor 4 may be a light detecting sensor or a PM 2.5 sensor.

Please refer to FIG. 1. The detecting compartment 12 further includes a connection through hole 126 allowing one end of a flexible circuit board 5 to penetrate therethrough and to be electrically connected with the actuator 3. The connection through hole 126 is sealed by using a potting compound after the flexible circuit board 5 and the actuator 3 are connected with each other, so as to prevent the air from entering the inlet compartment 122 through the connection through hole 126. In addition, the carrying partition 121 has an exposed portion 121a extended outwardly to the exterior of the main body 1. A connector 127 is disposed on the exposed portion 121a and electrically connected to another end of the flexible circuit board 5, so as to provide the carrying partition 121 and the flexible circuit board 5 with electric energy and signals. The carrying partition 121 may be a circuit board, but not limited thereto.

Continuing to refer to FIG. 1, when the air at a humidity level higher than 40% is inhaled from the exterior into the air guiding part 11, it is transported through the plurality of storage chambers 111 which are connected in serial to be heated and dehumidified. After the dehumidified air is at the humidity level ranged from 10% to 40%, the dehumidified air is transported into the detecting part 12 and transported to the detecting channel 21 as being driven by the actuator 3. The sensor 4 measures the concentration of suspended particles contained in the air transported to the detecting channel 21. Preferably but not exclusively, the air transported to the detecting part 12 is at the humidity level ranged from 20% to 30%.

Figure 3:
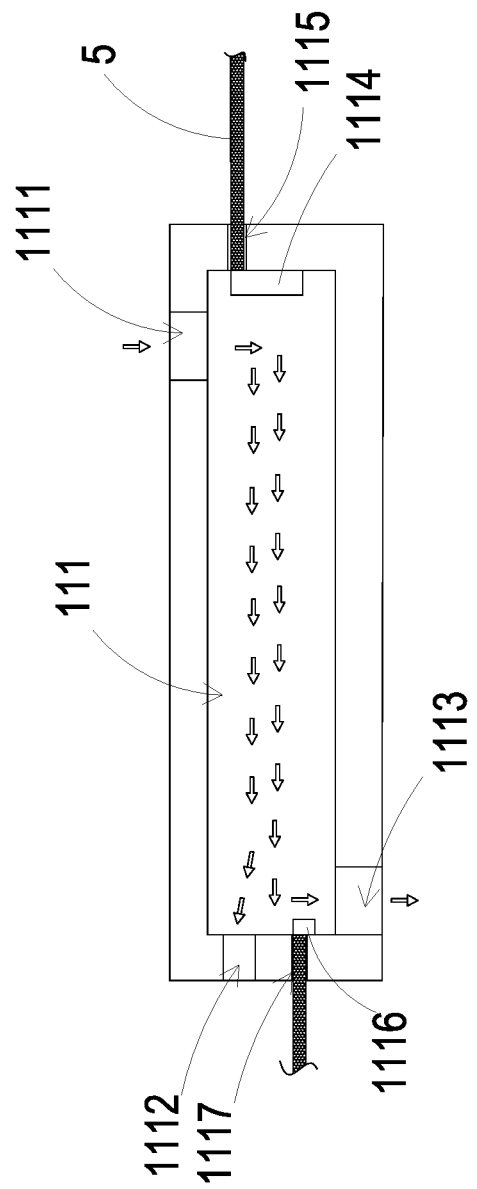
FIG. 3 is a schematic cross-sectional view illustrating the storage chamber according to the first embodiment of the present disclosure and take from a perspective opposite to that of FIG. 2.

Referring now to FIG. 3, the gas guiding part 11 includes a plurality of temperature and humidity sensors 1116 disposed within the storage chambers 111, respectively. In each storage chamber 111, the temperature and humidity sensor 1116 is configured to detect the temperature and the humidity of the air within the storage chamber 111, thereby adjusting a heating time and a heating power of the heating element 1114 of the storage chamber 111. In some embodiments, each storage chamber 111 further includes a first connection through hole 1115 and a second connection through hole 1117. The first connection through hole 1115 allows the flexible circuit board 5 to penetrate therethrough to be electrically connected with the heating element 1114. Meanwhile, the first connection through hole 1115 is sealed by using a potting compound so as to prevent the air from entering the storage chamber 111 through the first connection through hole 1115. Similarly, the second connection through hole 1117 allows the flexible circuit board 5 to penetrate therethrough to be electrically connected with the temperature and humidity sensor 1116. Meanwhile, the second connection through hole 1117 is sealed by using a potting compound so as to prevent the air from entering the storage chamber 111 through the second connection through hole 1117.

Figure 5:
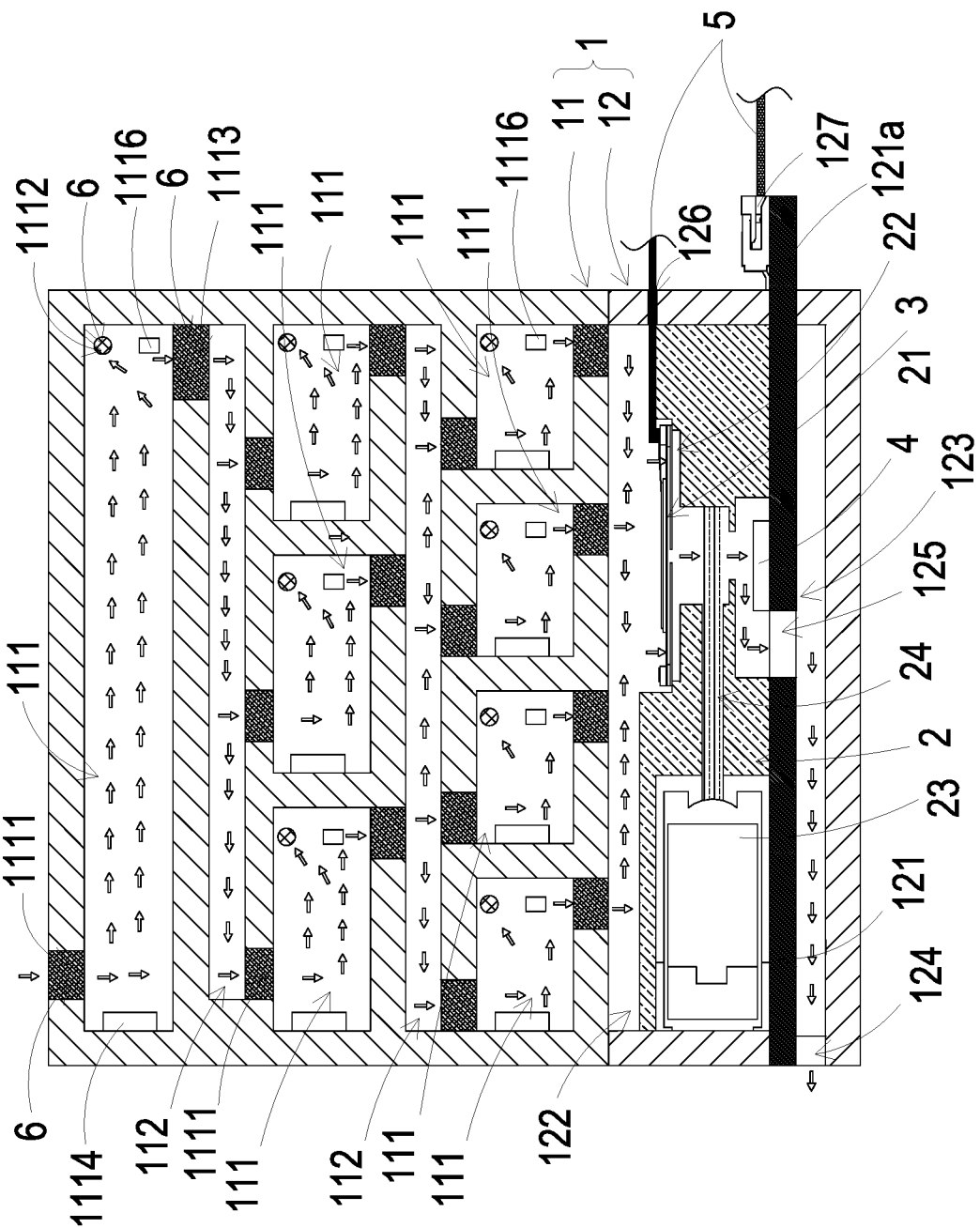
FIG. 5 is a schematic cross-sectional view illustrating the storage chambers with the valves according to the first embodiment of the present disclosure.

Please refer to FIG. 5. The air guiding part 11 further includes a plurality of valves 6 disposed on the inlet aperture 1111, the heat-dissipation aperture 1112 and the outlet aperture 1113 of each storage chamber 111, respectively, so as to control a communication state of the storage chamber 111 which is to perform heating and dehumidification operation. The valves 6 may be each controlled to be open or closed according to a detecting result of the temperature and humidity sensor 1116 of the corresponding storage chamber 111.

In the present disclosure, the air inhaled into the air guiding part 11 may be dehumidified in the ways described below.

According to a first aspect, the inlet apertures 1111, the heat-dissipation apertures 1112 and the outlet apertures 1113 of all the storage chambers 111 are opened by controlling the corresponding valves 6. When the air at the humidity level higher than 40% is inhaled into the air guiding part 11, it is transported through each of the plural storage chambers 111 which are connected in serial and in fluid communication with each other, thereby being dehumidified and heated for many times. In addition, in each of the storage chambers 111, the corresponding temperature and humidity sensor 1116 monitors the temperature and the humidity of the air therewithin, thereby adjusting a heating time and a heating power of the corresponding heating element 1114. Moreover, the water vapor generated by the heating and dehumidification operation in each storage chamber 111 is discharged out through the corresponding heat-dissipation aperture 1112. Then, the dehumidified air at the humidity level ranged from 10% to 40% is transported into the detecting part 12.

According to a second aspect, firstly, a single one of the storage chambers 111 is selected to perform the heating and dehumidification operation. By controlling the corresponding valves 6, the inlet aperture 1111 and the heat-dissipation aperture 1112 of said single one storage chamber 111 are opened and the outlet aperture 1113 of said single one storage chamber 111 is closed. Meanwhile, by controlling the corresponding valves 6, the inlet apertures 1111 and the outlet apertures 1113 of the rest of the storage chambers 111 are opened, and the heat-dissipation apertures of the rest of the storage chambers 111 are closed. When the air at the humidity level higher than 40% is inhaled to said single one storage chamber 111, the air is heated and dehumidified by the heating element 1114 of said single one storage chamber 111 and is monitored by the temperature and humidity sensor 1116 of said single one storage chamber 111. Once the temperature and humidity sensor 1116 of said single one storage chamber 111 determines that the humidity level of the air within said single one storage chamber 111 has met a required value, the outlet aperture 1113 of said single one storage chamber 111 is opened as the heating and dehumidification operation is considered to be finished. Thus, the dehumidified air at the humidity level ranged from 10% to 40% is directly guided into the detecting part 12 from said single one storage chamber 111 through the rest of the storage chambers 111, thereby achieving the heating and dehumidification operation in one single chamber.

According to a third aspect, firstly, a single one of the storage chambers 111 is selected to perform the heating and dehumidification operation. By controlling the corresponding valves 6, the inlet aperture 1111 and the heat-dissipation aperture 1112 of said single one storage chamber 111 are opened and the outlet aperture 1113 of said single one storage chamber 111 is closed. When the air at the humidity level higher than 40% is inhaled to said single one storage chamber 111, it is heated and dehumidified by the heating element 1114 of said single one storage chamber 111 and is monitored by the temperature and humidity sensor 1116 of said single one storage chamber 111. Once the temperature and humidity sensor 1116 determines that the humidity level of the air within said single one storage chamber 111 has met a first required value, the outlet aperture 1113 of said single one storage chamber 111 is opened and the dehumidified air is transported to another storage chamber 111 connected with said single one storage chamber 111 in serial. At this moment, by controlling the corresponding valves 6, the inlet aperture 1111 and the heat-dissipation aperture 1112 of said another storage chamber 111 are opened, and the outlet aperture 1113 of said another storage chamber 111 is closed. The dehumidified air transported into said another storage chamber 111 is heated and dehumidified again by the heating element 1114 of said another storage chamber 111. Similarly, once the temperature and humidity sensor 1116 of said another storage chamber 111 determines that the humidity level of the air within said another storage chamber 111 has met a second required value, the outlet aperture 1113 of said another storage chamber 111 is opened and the twice-dehumidified air is transported to further another storage chamber 111 connected with said another storage chamber 111 in serial to be heated and dehumidified for the third time, and so on. Thus, the air is heated and dehumidified in batches by the multiple storage chambers 111. Finally, the multiple-times-dehumidified air at the humidity level ranged from 10% to 40% is transported into the detecting part 12, thereby achieving the heating and dehumidification operations performed in a multiple-batch way.

The heating and dehumidification operations of the particle detecting module are described as the above. The structures and actions of the actuator 3 are described as the following.

Figure 6:
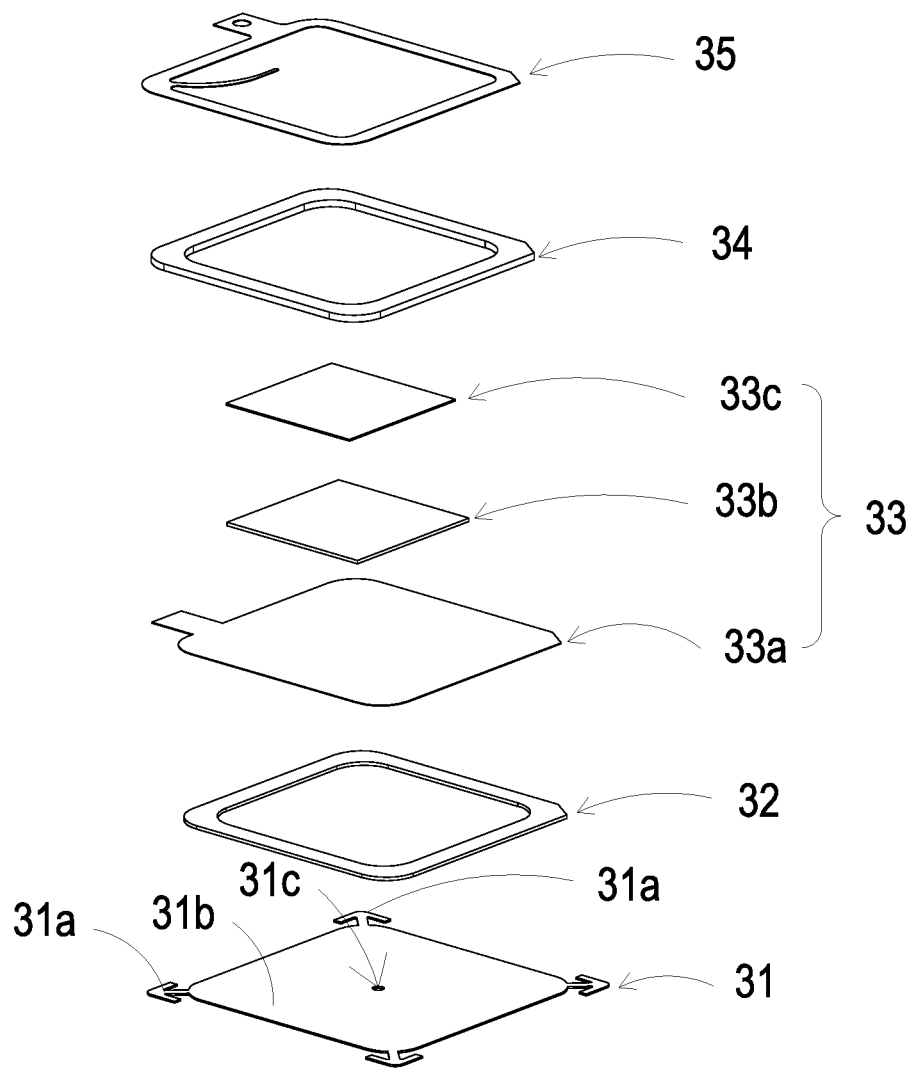
FIG. 6 is an exploded view illustrating the actuator according to the first embodiment of the present disclosure.

Please refer to FIGS. 6 to 7C. In the embodiment, the actuator 3 is a gas pump including a nozzle plate 31, a chamber frame 32, an actuation element 33, an insulation frame 34 and a conducting frame 35 stacked on each other sequentially. The nozzle plate 31 includes a plurality of connection components 31*a*, a suspension plate 31*b* and a central aperture 31*c*. The suspension plate 31*b* is permitted to undergo a bending vibration. The plurality of connection components 31*a* are connected to the edges of the suspension plate 31*b*. In some embodiments, there are four connection components 31*a* connected to four corners of the suspension plate 31*b*, respectively, but the present disclosure is not limited thereto. The central aperture 31*c* is formed at the center of the suspension plate 31*b*. The chamber frame 32 is carried and stacked on the suspension plate 31*b*. The actuation element 33 is carried and stacked on the chamber frame 32 and may include a piezoelectric carrying plate 33*a*, an adjusting resonance plate 33*b* and a piezoelectric plate 33*c*. The piezoelectric carrying plate 33*a* is carried and stacked on the chamber frame 32. The adjusting resonance plate 33*b* is carried and stacked on the piezoelectric carrying plate 33*a*. The piezoelectric plate 33*c* is carried and stacked on the adjusting resonance plate 33*b*. As the piezoelectric plate 33*c* is actuated by an applied voltage, the piezoelectric plate 33*c* deforms to drive the piezoelectric carrying plate 33*a* and the adjusting resonance plate 33*b* to bend and vibrate in the reciprocating manner. The insulation frame 34 is carried and stacked on the piezoelectric carrying plate 33*a* of the actuation element 33. The conducting frame 35 is carried and stacked on the insulation frame 34. A resonance chamber 36 is formed among the actuation element 33, the chamber frame 32 and the suspension plate 31*b*. The adjusting resonance plate 33*b* may be thicker than the piezoelectric carrying plate 33*a*.

Figure 7A:
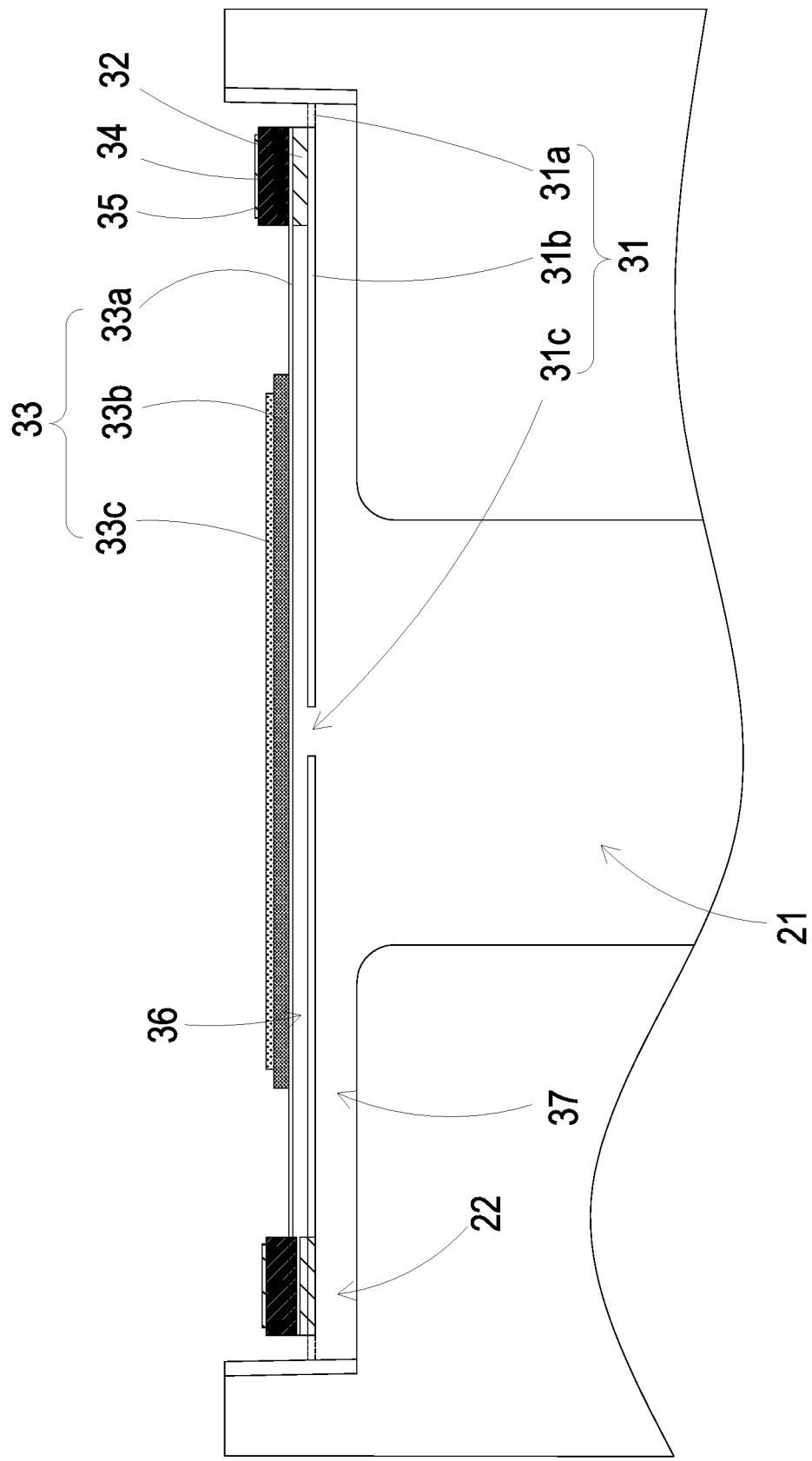
FIG. 7A is a schematic cross-sectional view illustrating the actuator according to the first embodiment of the present disclosure.

As shown in FIG. 7A, the actuator 3 is disposed within the receiving slot 22 of the fine particle detecting base 2 through the plurality of connection component 31*a* of the actuator 3. The nozzle plate 31 is spaced apart from the bottom surface of the receiving slot 22. An airflow chamber 37 is formed between the nozzle plate 31 and the receiving slot 22. As shown in FIG. 7B, when an voltage is applied to the piezoelectric plate 33*c* of the actuation element 33, the piezoelectric plate 33*c* is deformed by the piezoelectric effect, thereby simultaneously driving the adjusting resonance plate 33*b* and the piezoelectric carrying plate 33*a* to displace. More specifically, the nozzle plate 31 is driven to move due to the Helmholtz resonance effect, making the actuation element 33 displaced in a direction away from the bottom of the receiving slot 22. Since the actuation element 33 is displaced in a direction away from the bottom of the receiving slot 22, the volume of the airflow chamber 37 formed between the nozzle plate 31 and the bottom of the receiving slot 22 is expended and a negative pressure is formed in the airflow chamber 37. The air outside the actuator 3 is transported into the airflow chamber 37 through the vacant spaces formed among the plurality of connection components 31*a* of the nozzle plate 31 and the lateral walls of the receiving slot 22 due to the pressure gradient, whereby the airflow chamber 37 is pressurized. As shown in FIG. 7C, the air flows into the airflow chamber 37 continuously and a positive pressure is formed in the airflow chamber 37. At the meantime, the actuation element 33 is driven to vibrate in a direction toward the bottom of the receiving slot 22 in response to the voltage, so that the volume of the airflow chamber 37 is shrunken and the air contained in the airflow chamber 37 is compressed to flow into the detecting channel 21. Consequently, the sensor 4 can measure the concentration of the suspended particles contained in the air flowing through the detecting channel 21.

In some embodiments, the actuator 3 is a gas pump. In some other embodiments, the actuator 3 can be a microelectromechanical-systems gas pump formed by a microelectromechanical-systems method. The nozzle plate 31, the chamber frame 32, the actuation element 33, the insulation frame 34 and the conducting frame 35 can all be made through a surface micromachining technique to reduce the volume of the actuator 3.

Figure 8A:
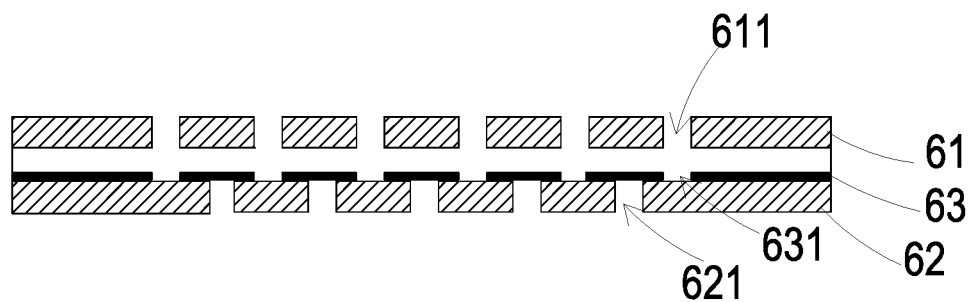
FIG. 8A is a schematic cross-sectional view illustrating the valve according to the first embodiment of the present disclosure.
Figure 8B:
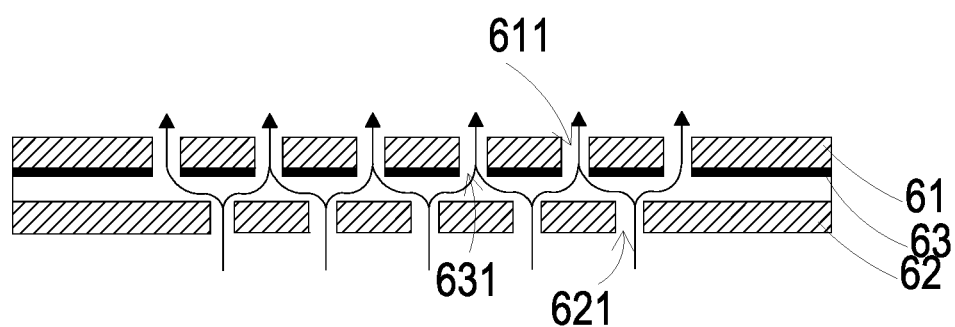
FIG. 8B is a schematic cross-sectional view illustrating action of valve according to the first embodiment of the present disclosure.

Please refer to FIGS. 8A and 8B. In the embodiment, the valve 6 includes a stationary component 61, a sealing component 62 and a displacement component 63. The displacement component 63 is disposed between the stationary component 61 and the sealing component 62 and capable of displacing therebetween. The stationary component 61 has a plurality of first orifices 611. The displacement component 63 has a plurality of second orifices 631 respectively corresponding in position to the plurality of first orifices 611 of the stationary component 61. That is, the plurality of first orifices 611 of the stationary component 61 are aligned with the plurality of second orifices 631 of the displacement component 63. The sealing component 62 has a plurality of third orifices 621. The plurality of third orifices 621 of the sealing component 62 are misaligned with the plurality of first orifices 611 of the stationary component 61. The stationary component 61, the sealing component 62 and the displacement component 63 of the valve 6 are controlled by connecting to a processor (not shown) through the flexible circuit board 5, so as to control the displacement component 63 to move toward the stationary component 61 and make the valve 6 in an open state.

In a first aspect of the valve 6 in the present disclosure, the displacement component 63 is made of a charged material, and the stationary component 61 is made of a bipolar conductive material. The stationary component 61 is electrically connected to the processor on the flexible circuit board 5, so as to control the polarity (positive electrical polarity or negative electrical polarity) of the stationary component 61. In case that the displacement component 63 is made of a negative-charged material, and the valve 6 needs to be controlled to open, the stationary component 61 is controlled to form a positive electrode. In that, the displacement component 63 and the stationary component 61 are maintained in the opposite polarity, so that the displacement component 63 moves toward the stationary component 61 and the valve 6 is in an open state (as shown in FIG. 8B). Alternatively, in case that the displacement component 63 is made of a negative-charged material, and the valve 6 needs to be controlled to close, the stationary component 61 is controlled to form a negative electrode. In that, the displacement component 63 and the stationary component 61 are maintained in the same polarity, and the displacement component 63 moves toward the sealing component 62 so that the valve 6 is in a closed state (as shown in FIG. 8A).

In a second aspect of the valve 6 in the present disclosure, the displacement component 63 is made of a magnetic material, and the stationary component 61 is made of an electromagnet material and can be controlled to change its magnetic polarity. The stationary component 61 is electrically connected to the processor on the flexible circuit board 5, so as to control the polarity (positive magnetic polarity or negative magnetic polarity) of the stationary component 61. In case that the displacement component 63 is made of a negative-magnetic material, and the valve 6 needs to be controlled to open, the stationary component 61 is controlled to form a positive-magnetic pole. In that, the displacement component 63 and the stationary component 61 are maintained in the opposite polarity, so that the displacement component 63 moves toward the stationary component 61 and the valve 6 is in an open state (as shown in FIG. 8B). Alternatively, in case that the displacement component 63 is made of a negative-magnetic material, and the valve 6 needs to be controlled to close, the stationary component 61 is controlled to form a negative-magnetic pole. In that, the displacement component 63 and the stationary component 61 are maintained in the same polarity, and the displacement component 63 moves toward the sealing component 62 so that the valve 6 is in a closed state (as shown in FIG. 8A).

Figure 9:
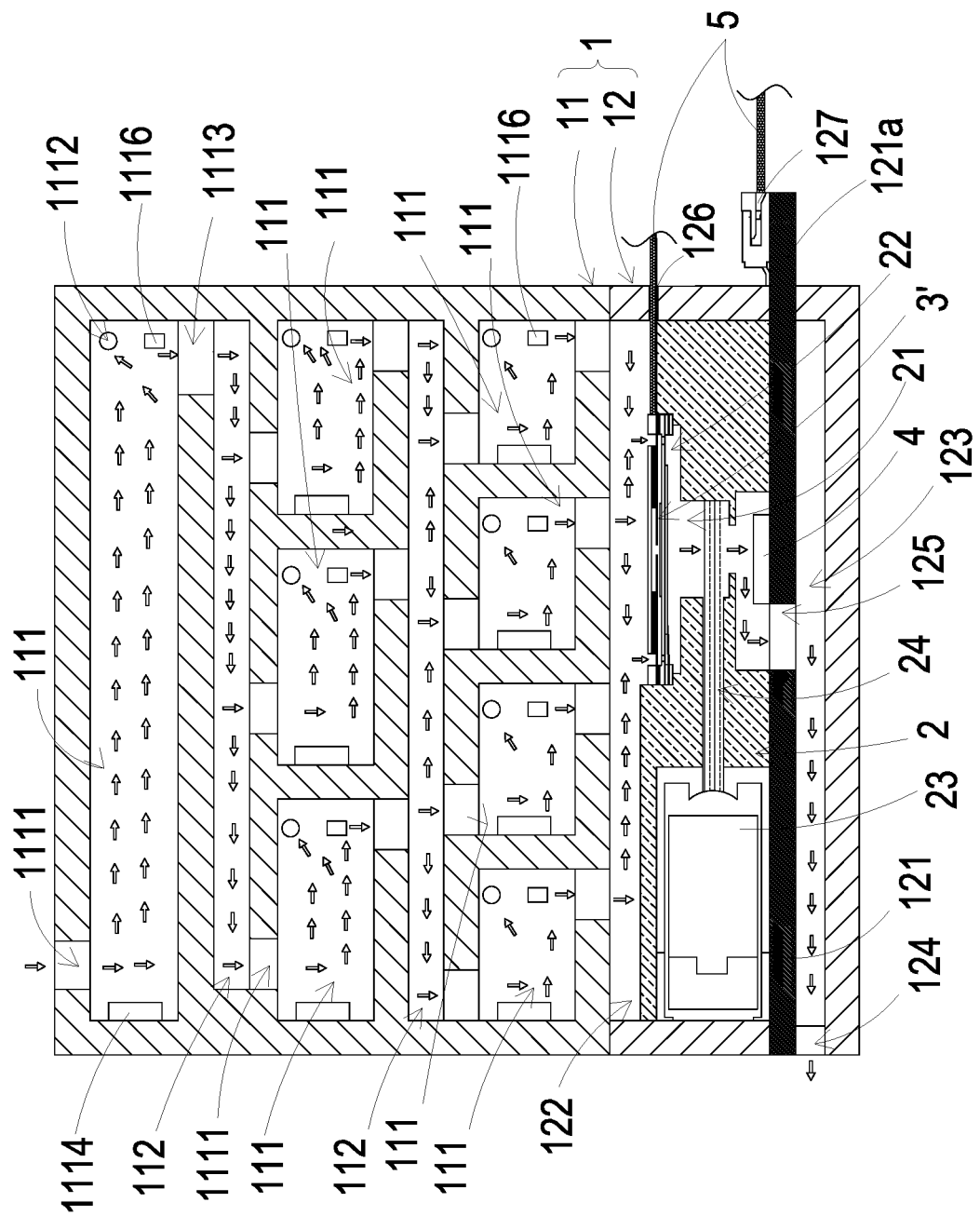
FIG. 9 is a schematic cross-sectional view illustrating a particle detecting module according to a second embodiment of the present disclosure.
Figure 10:
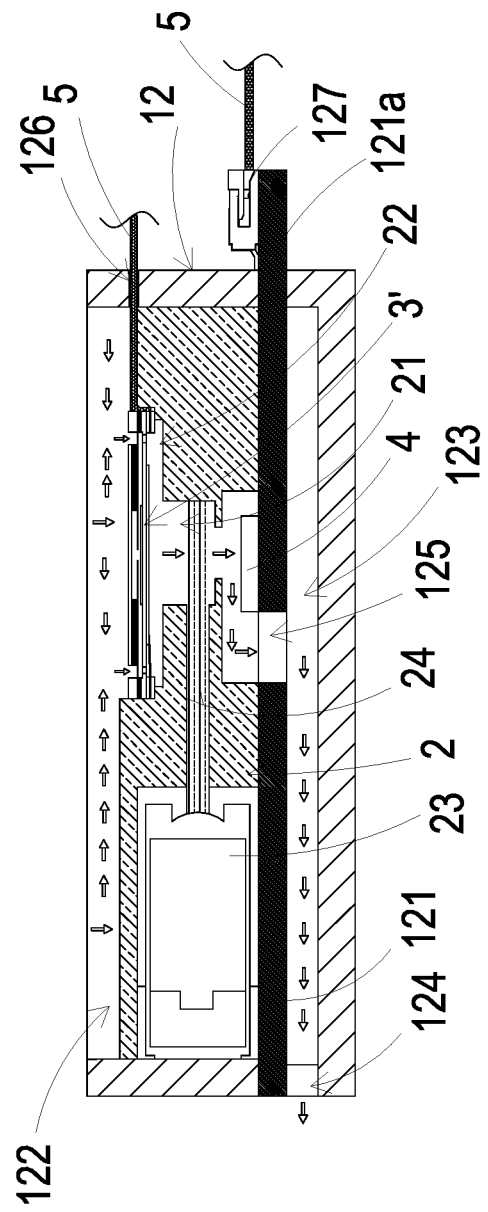
FIG. 10 is a schematic cross-sectional view illustrating the detecting part according to the second embodiment of the present disclosure.
Figure 11:
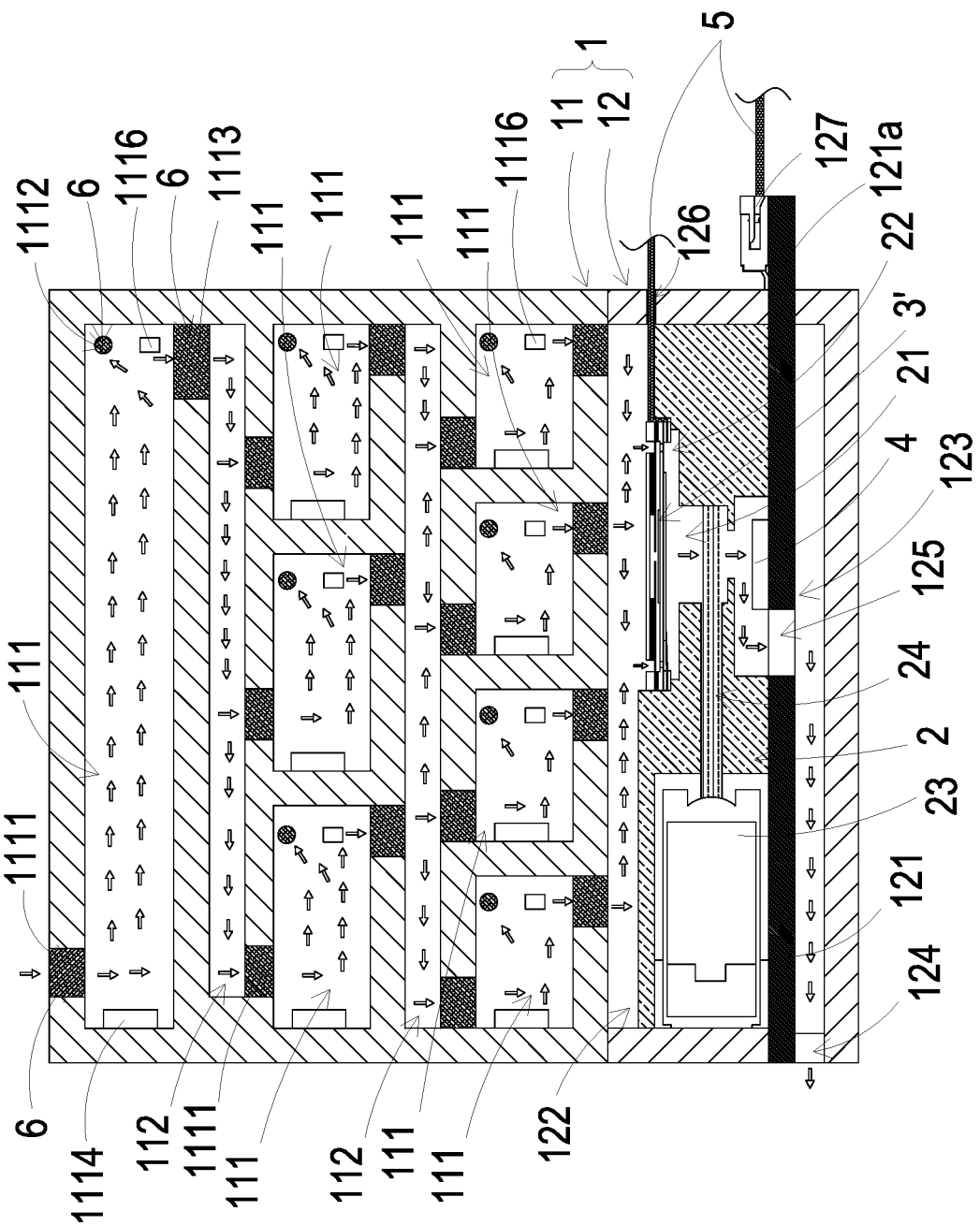
FIG. 11 is a schematic cross-sectional view illustrating the storage chambers with the valves according to the second embodiment of the present disclosure.

Please refer to FIGS. 9 to 11. FIG. 9 is a schematic cross-sectional view illustrating a particle detecting module according to a second embodiment of the present disclosure. FIG. 10 is a schematic cross-sectional view illustrating the detecting part according to the second embodiment of the present disclosure. FIG. 11 is a schematic cross-sectional view illustrating the storage chambers with the valves according to the second embodiment of the present disclosure. In the second embodiment, the structures, elements and functions of the particle detecting module are similar to those of the particle detecting module in the first embodiment and are not redundantly described herein. In the second embodiment, the structure and actions of the actuator 3' are different from those of the actuator 3 in the first embodiment. The structure and actions of the actuator 3' are described as the following.

Figure 12A:
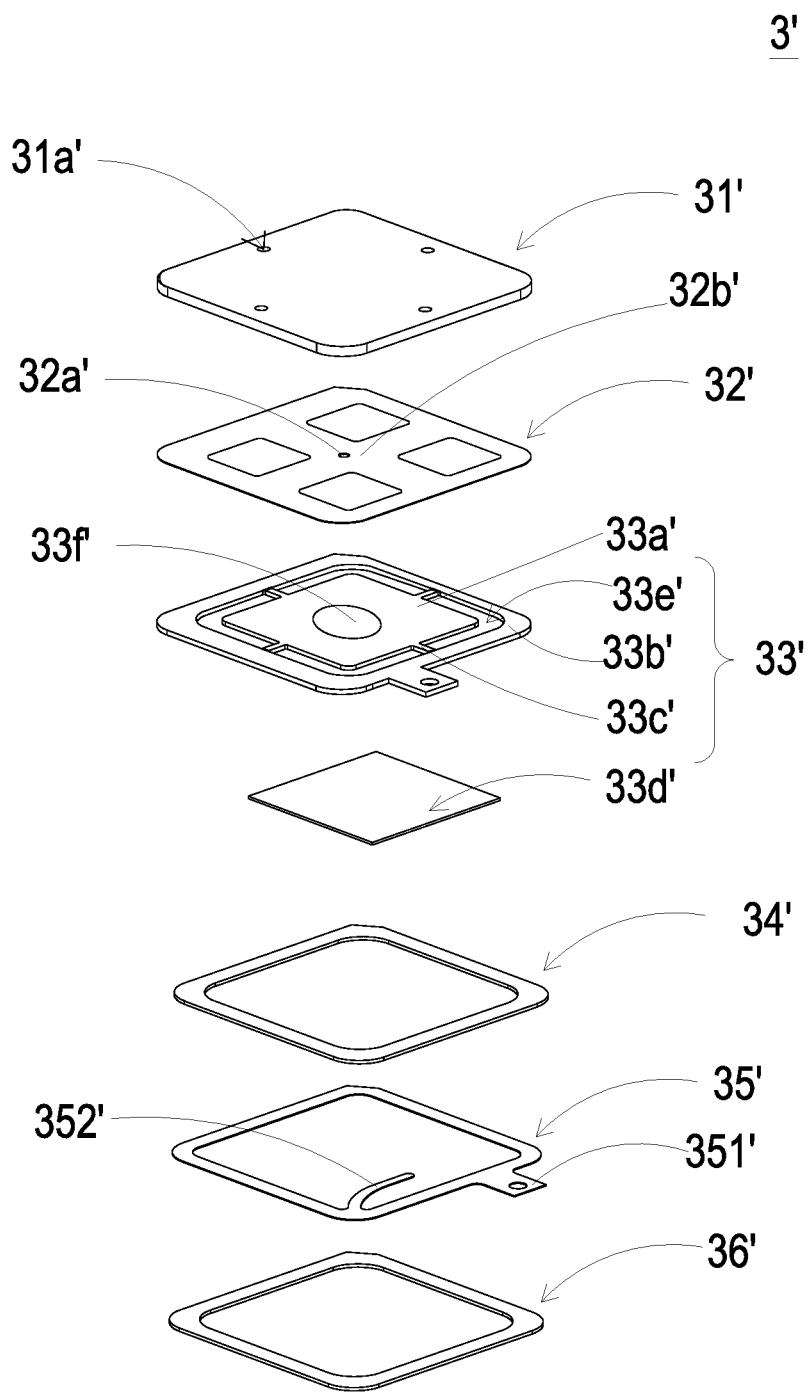
FIG. 12A is an exploded view illustrating the actuator according to the second embodiment of the present disclosure and taken from the bottom side.
Figure 12B:
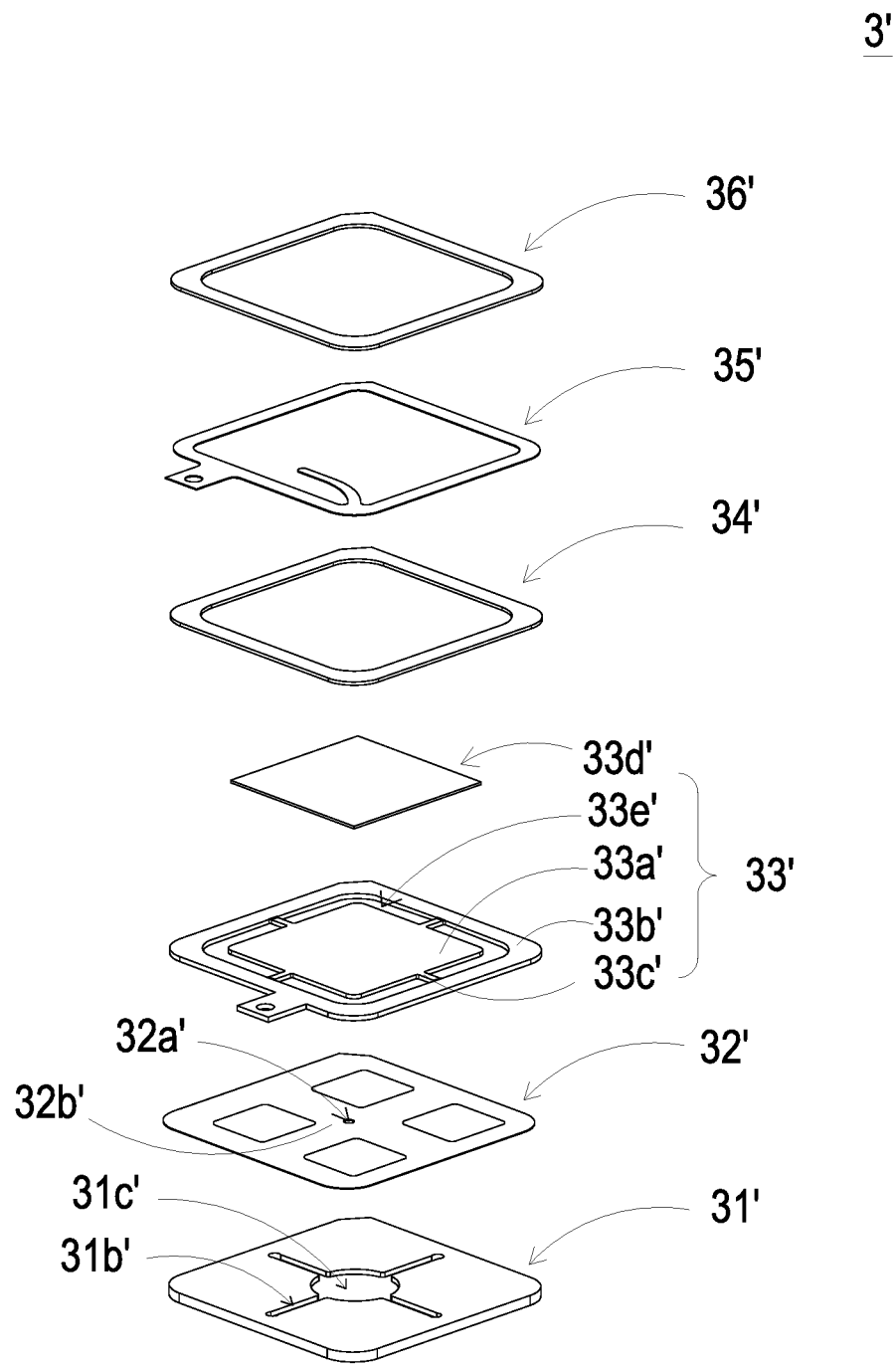
FIG. 12B is an exploded view illustrating the actuator according to the second embodiment of the present disclosure and taken from the top side.
Figure 13A:
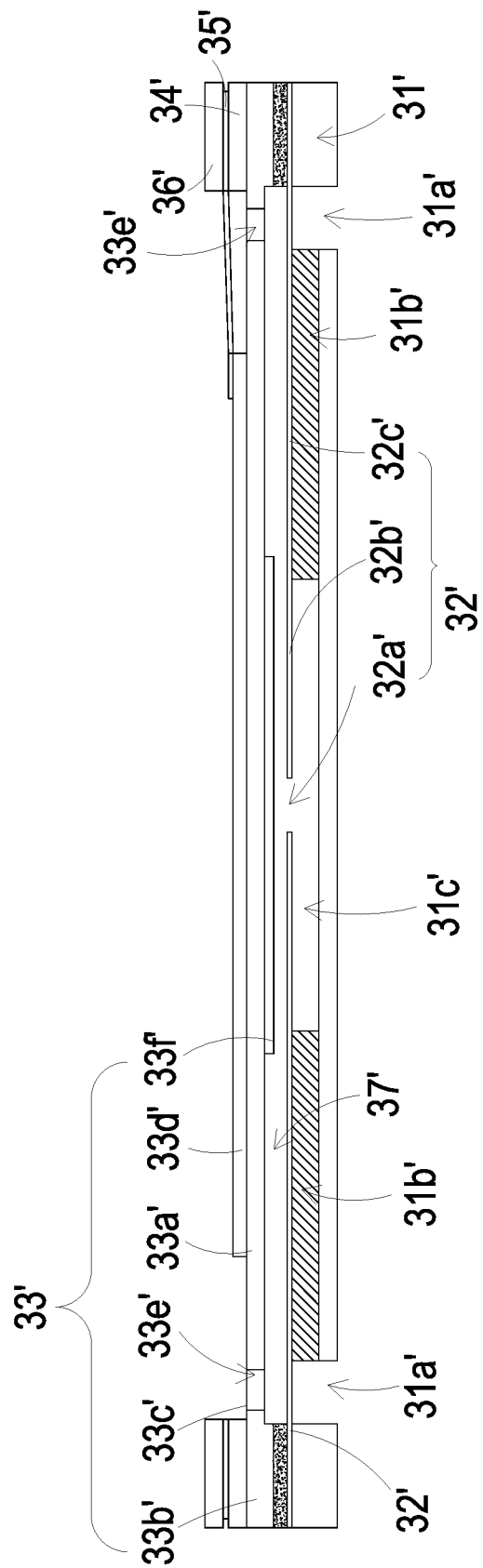
FIG. 13A is a schematic cross-sectional view illustrating the actuator according to the second embodiment of the present disclosure.

Please refer to FIGS. 12A, 12B and 13A. In the second embodiment, the actuator 3' is a gas pump and includes an air inlet plate 31', a resonance plate 32', a piezoelectric actuator 33', a first insulation plate 34', a conducting plate 35' and a second insulation plate 36'. The air inlet plate 31', the resonance plate 32', the piezoelectric actuator 33', the first insulation plate 34', the conducting plate 35' and the second insulation plate 36' are stacked and assembled sequentially.

In the second embodiment, the air inlet plate 31' has at least one inlet 31a', at least one convergence channel 31b' and a convergence chamber 31c'. The convergence channel 31b' is disposed and spatially corresponding to the inlet 31a'. The inlet 31a' allows the air to be inhaled therethrough. The air inhaled through the inlet 31a' is guided to the convergence chamber 31c' through the convergence channel 31b'. The resonance plate 32' has a central aperture 32a', a movable part 32b' and a fixed part 32c'. The central aperture 32a' is facing the convergence chamber 31c' of the air inlet plate 31'. The movable part 32b' surrounds the central aperture 32a'. The fixed part 32c' surrounds the outer edge of the movable part 32b'. A chamber space 37' is formed between the resonance plate 32' and the piezoelectric actuator 33'. Thus, when the actuator 3' is driven, the air is introduced from the inlet 31a' of the air inlet plate 31' and converged to the convergence chamber 31c' along the convergence channel 31b'. Then, the air flows through the central aperture 32a' of the resonance plate 32', and is further transported through a resonance between the piezoelectric actuator 33' and the movable part 32b' of the resonance plate 32' to achieve the air transportation.

Please refer to FIGS. 12A, 12B and 13A. In the second embodiment, the piezoelectric actuator 33' includes a suspension plate 33a', an outer frame 33b', at least one bracket 33c' and a piezoelectric element 33d'. The suspension plate 33a' is a square structure and permitted to undergo a bending vibration, but not limited thereto. The suspension plate 33a' has a bugle 33f'. In the embodiment, the suspension plate 33a' is designed as a square shape, because the square suspension plate 33a' is more power-saving than the circular suspension plate. Generally, the consumed power of the capacitive load at the resonance frequency is positively related to the resonance frequency. Since the resonance frequency of the square suspension plate 33a' is obviously lower than that of the circular square suspension plate, the consumed power of the square suspension plate 33a' is fewer. Certainly, in other embodiments, the shape of the suspension plate 33a' is adjustable according to the practical requirements. The outer frame 33b' is arranged around the suspension plate 33a'. The at least one bracket 33c' is connected between the suspension plate 33a' and the outer frame 33b' for elastically supporting the suspension plate 33a'. A length of a side of the piezoelectric element 33d' is smaller than or equal to a length of a side of the suspension plate 33a'. The piezoelectric element 33d' is attached on the surface of the suspension plate 33a' to drive the suspension plate 33a' to undergo the bending vibration in response to an applied voltage. At least one vacant space 33e' is formed among the suspension plate 33a', the outer frame 33b' and the bracket 33c' for the air flowing therethrough. The bulge 33f is convexly disposed on another surface of the suspension plate 33a'. In the embodiment, the bugle 33f is formed by etching process to form a one-piece structure, but not limited thereto.

Please refer to FIG. 13A. In the second embodiment, the chamber space 37' can be formed by filling the gap between the resonance plate 32' and the outer frame 33b' of the piezoelectric actuator 33' with a material, such as a conductive adhesive, but not limited thereto. Thus, a specific depth between the resonance plate 32' and the suspension plate 33a' is maintained to allow the air to flow rapidly. In addition, since the resonance plate 32' and the suspension plate 33a' are maintained at a suitable distance, so that the contact interference therebetween is reduced and the generated noise is largely reduced. In some other embodiments, the thickness of the conductive adhesive filled into the gap between the resonance plate 32' and the outer frame 33b' of the piezoelectric actuator 33' is reduced by increasing the height of the outer frame 33b' of the piezoelectric actuator 33'. In that, the suspension plate 33a' and the resonance plate 32' are maintained at a suitable distance and the thickness of conductive adhesive filled in the entire actuator 3' is not influenced due to the hot pressing temperature and the cooling temperature. It avoids that the actual size of the chamber space 37' is influenced due to the thermal expansion and contraction after the entire actuator 3' is assembled.

Figure 13B:
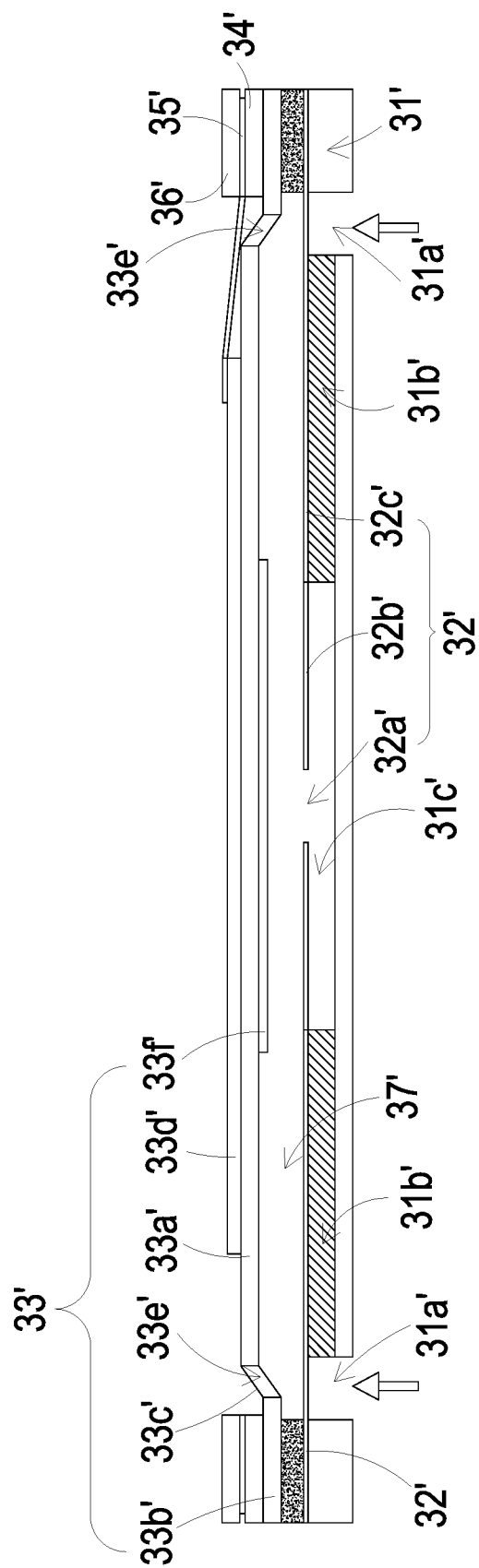
FIG. 13B is a schematic cross-sectional view illustrating the actuator according to a third embodiment of the present disclosure.

Please refer to FIG. 13B. According to a third embodiment, the suspension plate 33a' is formed by stamping to make it extend at a distance in a direction away from the resonance plates 32'. The extended distance can be adjusted through the at least one bracket 33c' formed between the suspension plate 33a' and the outer frame 33b'. Consequently, the top surface of the bulge 33f disposed on the suspension plate 33a' and the coupling surface the outer frame 33b' are non-coplanar. By utilizing a small amount of filling materials, such as a conductive adhesive applied to the coupling surface of the outer frame 313b, the piezoelectric actuator 33' is attached to the fixed part 32c' of the resonance plate 32' by heat pressing, thereby assembling the piezoelectric actuator 33' and the resonance plates 32' in combination. Thus, the structure of the chamber space 37' is improved by directly stamping the suspension plate 33a' of the piezoelectric actuator 33' described above. In this way, the required chamber space 37' can be achieved by adjusting the stamping distance of the suspension plate 33a' of the piezoelectric actuator 33'. It benefits to simplify the structural design of the chamber space 37', and also achieves the advantages of simplifying the process and shortening the processing time.

Please refer to FIGS. 12A and 12B again. In the second embodiment, the first insulation plate 34', the conducting plate 35' and the second insulation plate 36' are all thin frame-shaped sheets, but not limited thereto. The air inlet plate 31', the resonance plate 32', the piezoelectric actuator 33', the first insulation plate 34', the conducting plate 35' and the second insulation plate 36' can all be made through a surface micromachining technique to reduce the volume of the actuator 3' and form a micro-electromechanical-systems actuator 3'.

Figure 13C:
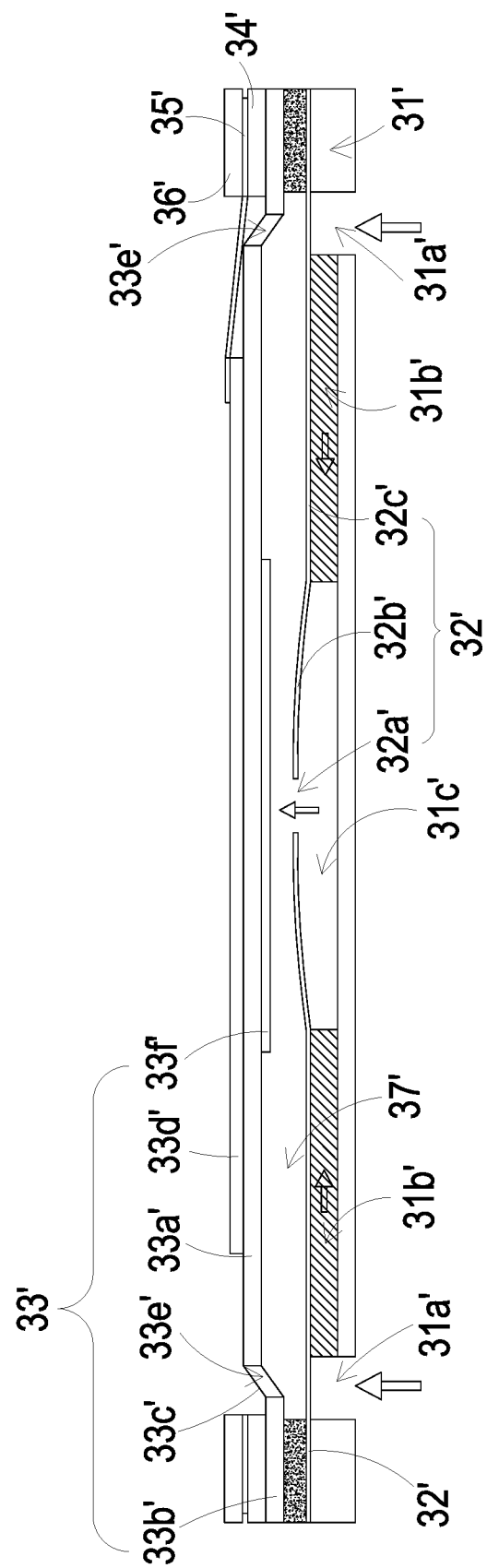
FIGS. 13C to 13E are schematic views illustrating actions of the actuator according to the second embodiment of the present disclosure.

Please refer to FIG. 13C. In respect to actions of the piezoelectric actuator 33', when the piezoelectric element 33d' of the piezoelectric actuator 33' is deformed in response to an applied voltage, the suspension plate 33a' is driven to displace in the direction away from the air inlet plate 31'. In that, the volume of the chamber space 37' is increased, a negative pressure is formed in the chamber space 37', and the air in the convergence chamber 31c' is inhaled into the chamber space 37'. At the same time, the resonance plate 32' is in resonance and thus displaced synchronously in the direction away from the air inlet plate 31'. Thereby, the volume of the convergence chamber 31c' is increased. Since the air in the convergence chamber 31c' flows into the chamber space 37', the convergence chamber 31c' is also in a negative pressure state, and the air is sucked into the convergence chamber 31c' by flowing through the inlet 31a' and the convergence channel 31b'.

Figure 13D:
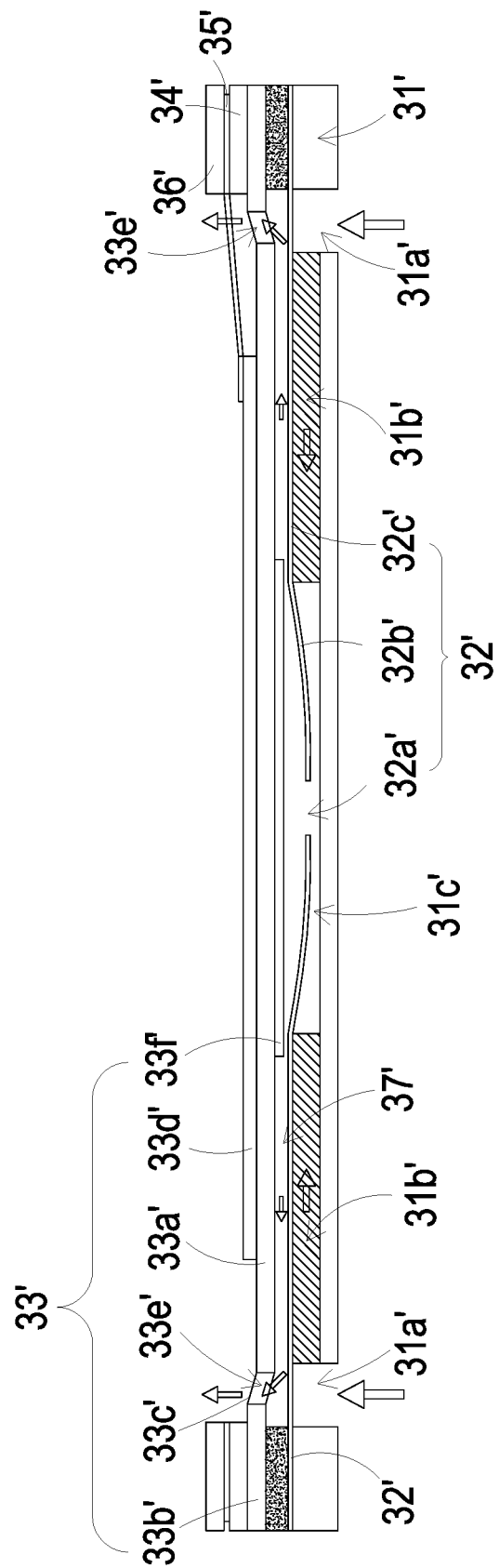

Then, as shown in FIG. 13D. The piezoelectric element 33d' drives the suspension plate 33a' to be displaced toward the air inlet plate 31' to compress the chamber space 37'. Similarly, the resonance plate 32' is actuated in resonance by the suspension plate 33a' and displaced toward the air inlet plate 31'. Thus, the air contained in the chamber space 37' is further transported to flow through the vacant spaces 33e' in the direction away from the air inlet plate 31' and it achieves the effect of air transportation.

Figure 13E:
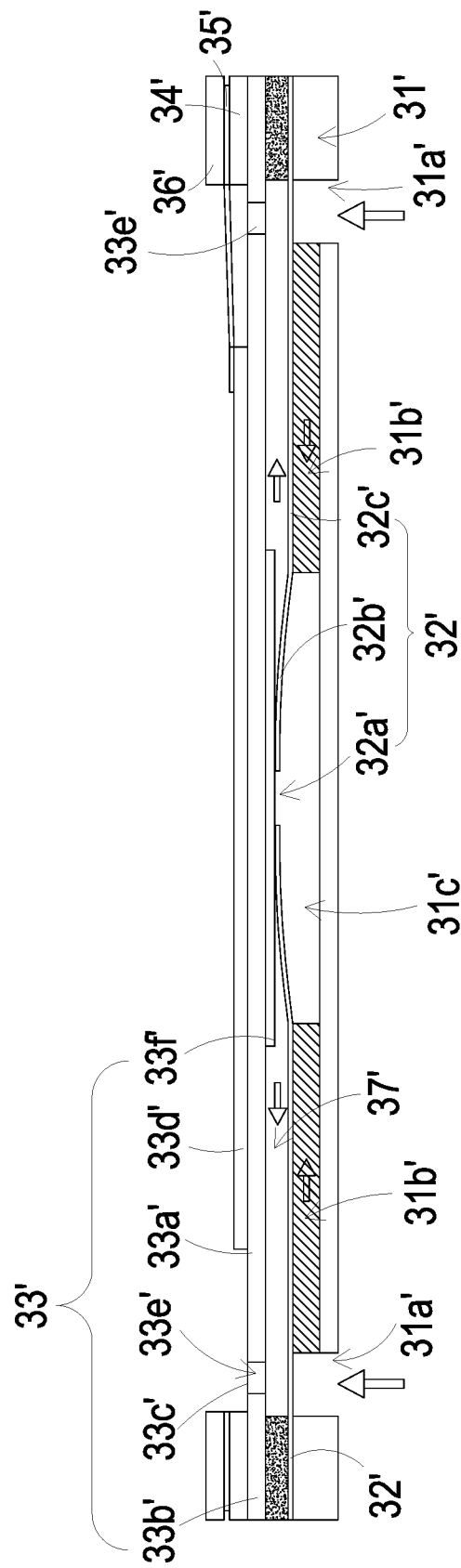

Finally, as shown in FIG. 13E. When the suspension plate 33a' is driven to return the initial state and not displaced by the piezoelectric element 33d', the resonance plate 32' is also driven to displace in the direction away from the air inlet plate 31' at the same time. In that, the resonance plate 32' pushes the air in the chamber space 37' toward the vacant space 33e', and the volume of the convergence chamber 31c' is increased. Thus, the air can continuously flow through the inlet 31a' and the convergence channel 31b' and be converged in the convergence chamber 31c'. By repeating the actions of FIGS. 13C to 13E continuously, the actuator 3' can continuously transport the air at high speed. It achieves the transporting and outputting operations of actuator 3'.

Moreover, please refer to FIGS. 12A and 12B. A conducting pin 351' is protruding outwardly from the outer edge of the conducting plate 35' and an electrode 352' is curvedly protruded from the inner edge of the conducting plate 35'. The electrode 352' is electrically connected to the piezoelectric element 33d' of the piezoelectric actuator 33'. The conducting pin 351' is outwardly connected to external current, thereby diving the piezoelectric element 33d' of the piezoelectric actuator 33'. In addition, with the arrangements of the first insulation plate 34' and the second insulation plate 36', it avoids the occurrence of short circuit.

In summary, the present disclosure provides a particle detecting module. By utilizing the heating elements disposed within the plurality of storage chambers, the air transported from the air guiding part to the detecting part is maintained at the humidity level ranged from 10% to 40%. The air maintained at the humidity level ranged from 10% to 40% is transported from the inlet compartment into the detecting channel as being driven by the actuator for measuring sizes and concentrations of suspended particles. By maintaining the standard humidity to improve the detecting efficiency of suspended particles, the effects of detecting the suspended particles are further improved. In addition, the particle detecting module of the present disclosure can be applied to a thin-type portable device for detecting suspended particles. With the habit of carrying portable devices with modern people, the particle detecting module can be actually introduced into the thin-type portable device to achieve the purpose of detecting suspended particles at anytime and anywhere.

While the disclosure has been described in terms of what is presently considered to be the most practical and preferred embodiments, it is to be understood that the disclosure needs not be limited to the disclosed embodiments. On the contrary, it is intended to cover various modifications and similar arrangements included within the spirit and scope of the appended claims which are to be accorded with the broadest interpretation so as to encompass all such modifications and similar structures.

What is claimed is:

1. A particle detecting module comprising:
   a main body comprising:
   an air guiding part, comprising:
   a plurality of storage chambers; each of which comprises an inlet aperture, a heat-dissipation aperture, an outlet aperture and a heating element, wherein the heating element is configured to heat and dehumidify the air within the storage chamber, the water vapor generated thereby is discharged out from the storage chamber through the heat-dissipation aperture and the dehumidified air is guided out from the storage chamber through the outlet aperture;
   a plurality of airflow channels, wherein each two adjacent storage chambers are in fluid communication with each other through a corresponding one of the airflow channels, so that after the air in each storage chamber is dehumidified, the dehumidified air is guided to an adjacent storage chamber through the corresponding airflow channel to be dehumidified again;
   a plurality of temperature and humidity sensors, each of which is disposed within each of the plurality of storage chambers, respectively, to detect the temperature and the humidity of the air within the corresponding storage chamber, thereby adjusting a heating time and a heating power of the heating element of the corresponding storage chamber; and
   a plurality of valves disposed on the inlet aperture, the heat-dissipation aperture and the outlet aperture of each of the plurality of storage chambers, respectively, so as to control a communication state of each storage chamber which is to perform a heat and dehumidification operation, wherein each of the valves is controlled to be opened or closed according to a detecting result of the temperature and humidity sensor of the corresponding storage chamber; and
   a detecting part combined with the air guiding part, comprising:
   a carrying partition dividing an inner space of the detecting part into an inlet compartment and an outlet compartment, and having a communication opening in fluid communication between the inlet compartment and the outlet compartment; and
   a discharging aperture in fluid communication between the outlet compartment and the exterior of the main body;
   a fine particle detecting base disposed in the inlet compartment and having a detecting channel and a receiving slot, wherein the receiving slot is located at one end of the detecting channel to be in fluid communication therewith;
   an actuator disposed in the fine particle detecting base and configured to guide the air to flow in one way in the detecting part, wherein the air is guided to flow from the inlet compartment into the detecting channel, then being guided to the outlet compartment through the communication opening and discharged out through the discharging aperture; and
   a sensor disposed on the carrying partition and located in the detecting channel of the fine particle detecting base, the sensor being configured to measure a concentration of suspended particles contained in the air in the detecting channel,
   wherein when air at a humidity level higher than 40% is guided from the exterior into the air guiding part, the air is transported through each of the plurality of storage chambers connected in serial to be heated and dehumidified to achieve the humidity level ranged from 10% to 40%, after which the dehumidified air is transported into the detecting part and transported to the detecting channel through the actuator, and the concentration of suspended particles contained therein is detected by the sensor.

2. The particle detecting module according to claim 1, wherein the air transported to the detecting part is at the humidity level ranged from 20% to 30%.

3. The particle detecting module according to claim 1, wherein the inlet apertures, the outlet apertures and the heat-dissipation apertures of the storage chambers which are to perform the heat and dehumidification operation are opened by controlling the corresponding valves, so that when the air at the humidity level higher than 40% is guided from the exterior into the air guiding part, the air passes through each of the storage chambers to be heated and dehumidified for several times while water vapor generated thereby is discharged out from each of the storage chambers through the heat-dissipation aperture thereof, after which the dehumidified air at the humidity level ranged from 10% to 40% is transported into the detecting part.

4. The particle detecting module according to claim 1, wherein by controlling the corresponding valves, the inlet aperture and the heat-dissipation aperture of a single one of the storage chambers which is to perform the heat and dehumidification operation are opened and the outlet aperture thereof is closed, while the inlet apertures and the outlet apertures of the rest of the storage chambers are opened and the heat-dissipation apertures thereof are closed, so that when the air at the humidity level higher than 40% is guided from the exterior into the single one storage chamber, the air is heated and dehumidified by the heating element thereof, wherein once the temperature and humidity, sensor of the single one storage chamber determines that the humidity level of the air within the single one storage chamber has met a required value, the outlet aperture of the single one storage chamber is opened and the dehumidified air therein at the humidity level ranged from 10% to 40% is transported through the rest of the storage chambers into the detecting part.

5. The particle detecting module according to claim 1, wherein the inlet aperture and the heat-dissipation aperture of a single one of the storage chambers which is to perform the heat and dehumidification operation are opened and the outlet aperture thereof is closed by controlling the corresponding valves, so that when the air at the humidity level higher than 40% is guided from the exterior into the single one storage chamber, the air is heated and dehumidified by the heating element thereof, wherein once the temperature and humidity sensor of the single one storage chamber determines that the humidity level of the air within the single one storage chamber has met a first required value, the outlet aperture of the single one storage chamber is opened and the dehumidified air is guided to another one of the storage chambers connected to the single one storage chamber in serial to be heated and dehumidified again, while the inlet aperture and the heat-dissipation aperture of the another storage chamber are opened and the outlet aperture thereof is closed, wherein once the temperature and humidity sensor of the another storage chamber determines that the humidity level of the air within the another storage chamber has met a second required value, the outlet aperture of the another storage chamber is opened and the twice-dehumidified air is guided to further another one of the storage chambers connected to the another storage chamber in serial to be heated and dehumidified repeatedly, so that the air is heated and dehumidified in batches by the multiple ones of the storage chambers, after which the air at the humidity level ranged from 10% to 40% is transported into the detecting part.

6. The particle detecting module according to claim 5, wherein the sensor is a PM 2.5 sensor.

7. The particle detecting module according to claim 1, wherein the actuator is a micro-electromechanical-systems gas pump.

8. The particle detecting module according to claim 1, wherein the actuator is a gas pump comprising:
a nozzle plate comprising:
a suspension plate permitted to undergo a bending vibration;
a plurality of connection components connected with the edges of the suspension plate to elastically support the suspension plate; and
a central aperture formed at the center of the suspension plate,
wherein the actuator is disposed within the receiving slot of the fine particle detecting base through the plurality of connection components as an airflow chamber is formed between the nozzle plate and the receiving slot, and at least one vacant space is formed among the plurality of connection components and the suspension plate;
a chamber frame carried and stacked on the suspension plate;
an actuation element carried and stacked on the chamber frame, wherein the actuation element is configured to bend and vibrate in a reciprocating manner in response to an applied voltage;
an insulation frame carried and stacked on the actuation element; and
a conducting frame carried and stacked on the insulation frame;
wherein a resonance chamber is formed among the actuation element, the chamber frame and the suspension plate, wherein when the actuation element is actuated, resonance between the actuation element and the nozzle plate occurs and the suspension plate of the nozzle plate vibrates in a reciprocating manner, thereby making the air flow through the at least one vacant space into the airflow chamber and enter the detecting channel to achieve air transportation.

9. The particle detecting module according to claim 8, wherein the actuation element comprises:
a piezoelectric carrying plate carried and stacked on the chamber frame;
an adjusting resonance plate carried and stacked on the piezoelectric carrying plate; and
a piezoelectric plate carried and stacked on the adjusting resonance plate, wherein the piezoelectric plate is configured to drive the piezoelectric carrying plate and the adjusting resonance plate to bend and vibrate in the reciprocating manner in response to the applied voltage.

10. The particle detecting module according to claim 9, wherein the adjusting resonance plate is thicker than the piezoelectric carrying plate.

11. The particle detecting module according to claim 4, wherein the actuator is a gas pump comprising:
an air inlet plate having at least one inlet, at least one convergence channel and a convergence chamber, wherein the at least one inlet allows the air to be introduced in, and the at least one convergence channel is spatially corresponding to the at least one inlet and guides the air from the inlet toward the convergence chamber;
a resonance plate having a central aperture and a movable part, wherein the central aperture is facing the convergence chamber and the movable part surrounds the central aperture; and
a piezoelectric actuator spatially corresponding to the resonance plate;
wherein the air inlet plate, the resonance plate and the piezoelectric actuator are stacked sequentially and a chamber space is formed between the resonance plate and the piezoelectric actuator, wherein resonance between the piezoelectric actuator and the resonance plate occurs when the piezoelectric actuator is actuated, thereby achieving air transportation as the air from the at least one inlet of the air inlet plate is converged to the convergence chamber along the at least one convergence channel and flows into the chamber space through the central aperture of the resonance plate.

12. The particle detecting module according to claim 11, wherein the piezoelectric actuator comprises:
a suspension plate having a square structure and permitted to undergo a bending vibration;
an outer frame arranged around the suspension plate;
at least one bracket connected between the suspension plate and the outer frame for elastically supporting the suspension plate; and
a piezoelectric element, wherein a length of a side of the piezoelectric element is smaller than or equal to a length of a side of the suspension plate, and the piezoelectric element is attached on a surface of the suspension plate to drive the suspension plate to undergo the bending vibration in response to an applied voltage.

13. The particle detecting module according to claim 11, wherein the actuator further comprises a conducting plate, a first insulation plate and a second insulation plate, wherein the air inlet plate, the resonance plate, the piezoelectric actuator, the first insulation the conducting plate and the second insulation plate are stacked sequentially.

14. The particle detecting module according to claim 1, wherein the carrying partition is a circuit board.

15. The particle detecting module according to claim 14, wherein the fine particle detecting base and the sensor are in electrical connection with the carrying partition, and the fine particle detecting base comprises a laser emitter electrically connected to the carrying partition and a light-beam channel in communication with the detecting channel to allow a light beam emitted by the laser emitter to irradiate an inner space of the detecting channel, so that the suspended particles in the detecting channel are irradiated to generate scattering light spots projected on the sensor to be measured.

16. A particle detecting module comprising:
at least one main body comprising:
at least one air guiding part, comprising:
a plurality of storage chambers, each of which comprises at least one inlet aperture, at least one heat-dissipation aperture, at least one outlet aperture and at least one heating element, wherein the heating element is configured to heat and dehumidify the air within the storage chamber, the water vapor generated thereby is discharged out from the storage chamber through the heat-dissipation aperture and the dehumidified air is guided out from the storage chamber through the outlet aperture;

a plurality of airflow channels, wherein each two adjacent storage chambers are in fluid communication with each other through a corresponding one of the airflow channels, so that after the air in each storage chamber is dehumidified, the dehumidified air is guided to an adjacent storage chamber through the corresponding airflow channel to be dehumidified again;

a plurality of temperature and humidity sensors, each of which is disposed within each of the plurality of storage chambers, respectively, to detect the temperature and the humidity of the air within the corresponding storage chamber, thereby adjusting a heating time and a heating power of the heating element of the corresponding storage chamber; and a plurality of valves disposed on the inlet aperture, the heat-dissipation aperture and the outlet aperture of each of the plurality of storage chambers, respectively, so as to control a communication state of each storage chamber which is to perform a heat and dehumidification operation, wherein each of the valves is controlled to be opened or closed according to a detecting result of the temperature and humidity sensor of the corresponding storage chamber; and at least one detecting part combined with the air guiding part, comprising:

at least one carrying partition dividing an inner space of the detecting part into at least one inlet compartment and at least one outlet compartment, and having at least one communication opening in fluid communication between the inlet compartment and the outlet compartment; and at least one discharging aperture in fluid communication between the outlet compartment and the exterior of the main body;

at least one fine particle detecting base disposed in the inlet compartment and having at least one detecting channel and at least one receiving slot, wherein the receiving slot is located at one end of the detecting channel to be in fluid communication therewith;

at least one actuator disposed in the fine particle detecting base and configured to guide the air to flow in one way in the detecting part, wherein the air is guided to flow from the inlet compartment into the detecting channel, then being guided to the outlet compartment through the communication opening and discharged out through the discharging aperture; and at least one sensor disposed on the carrying partition and located in the detecting channel of the fine particle detecting base, the sensor being configured to measure a concentration of suspended particles contained in the air in the detecting channel, wherein when air at a humidity level higher than 40% is guided from the exterior into the air guiding part, the air is transported through each of the plurality of storage chambers connected in serial to be heated and dehumidified to achieve the humidity level ranged from 10% to 40%, after which the dehumidified air is transported into the detecting part and transported to the detecting channel through the actuator, and the concentration of suspended particles contained therein is detected by the sensor.

\* \* \* \* \*